(12) United States Patent
Perler et al.

(10) Patent No.: US 10,874,385 B2
(45) Date of Patent: Dec. 29, 2020

(54) SURGICAL RETRACTOR

(71) Applicant: INMOTUS MEDICAL LLC, Carmel, IN (US)

(72) Inventors: Adam D. Perler, St. Petersburg, FL (US); James A. Zoellner, Avon, IN (US)

(73) Assignee: INMOTUS MEDICAL LLC, Carmel, IN (US)

( * ) Notice: Subject to any disclaimer, the term of this patent is extended or adjusted under 35 U.S.C. 154(b) by 11 days.

(21) Appl. No.: 16/154,686

(22) Filed: Oct. 8, 2018

(65) Prior Publication Data

US 2019/0038273 A1 Feb. 7, 2019

Related U.S. Application Data

(63) Continuation-in-part of application No. 14/876,747, filed on Oct. 6, 2015, now Pat. No. 10,092,281.

(51) Int. Cl.
*A61B 17/02* (2006.01)
*A61B 90/30* (2016.01)
*A61B 17/00* (2006.01)

(52) U.S. Cl.
CPC .......... *A61B 17/0206* (2013.01); *A61B 17/02* (2013.01); *A61B 90/30* (2016.02); *A61B 2017/00407* (2013.01); *A61B 2017/00424* (2013.01); *A61B 2017/00477* (2013.01); *A61B 2017/00734* (2013.01); *A61B 2090/309* (2016.02)

(58) Field of Classification Search
CPC ... A61B 17/02; A61B 17/0206; A61B 17/025; A61B 2017/00407
See application file for complete search history.

(56) References Cited

U.S. PATENT DOCUMENTS

| | | | | |
|---|---|---|---|---|
| 5,630,828 A * | 5/1997 | Mawhirt | ............ | A61B 5/15142 606/187 |
| 7,229,408 B2 * | 6/2007 | Douglas | .................... | A61B 1/32 600/214 |
| 7,276,024 B1 * | 10/2007 | Royse | .................... | A61B 17/02 600/210 |
| 8,257,256 B1 * | 9/2012 | Krolman | ............ | A61B 17/0231 600/236 |
| 8,317,693 B2 * | 11/2012 | Grey | ...................... | A61B 90/35 600/212 |
| 2016/0151058 A1 * | 6/2016 | Ferro | ..................... | A61B 17/02 600/215 |

* cited by examiner

*Primary Examiner* — Ellen C Hammond
(74) *Attorney, Agent, or Firm* — David Meibos; Maywood IP Law

(57) ABSTRACT

The surgical retractors and methods disclosed herein are designed to retract tissues in an ergonomic and anatomically correct manner by matching tissue curvatures in order to minimize tissue damage and reduce incision sizes. In one embodiment, a surgical retractor may include a first blade with proximal and distal ends, and a second blade with proximal and distal ends. The distal end of the first blade may be pivotally coupled to the distal end of the second blade. The surgical retractor may also include a ratcheting mechanism that is configured to maintain a selected distance between the proximal end of the first blade and the proximal end of the second blade.

18 Claims, 30 Drawing Sheets

SURGICAL RETRACTOR

CROSS-REFERENCE TO RELATED APPLICATIONS

The present application is a continuation-in-part of U.S. patent application Ser. No. 14/876,747 entitled "SURGICAL RETRACTOR" which was filed on Oct. 6, 2015. The foregoing is incorporated by reference as though set forth herein in its entirety.

TECHNICAL FIELD

The present disclosure relates to surgical retractors and devices for stabilizing tissue during a surgical procedure and, particularly, to surgical retractors for use in the lower extremity, upper extremity, abdominal, rectal, and other areas of the body during a surgical procedure.

BACKGROUND

Many surgical procedures utilize one or more surgical devices to retract tissue at a surgical site. Such surgical devices are generally known as surgical retractors. A wide variety of surgical retractors have been developed for general and/or specific use cases. However, many of these surgical retractors can fail to provide certain advantages, including, but not limited to: (1) providing a less complicated and more safe surgical procedure that can reduce the risk of nerve damage; (2) the ability to adapt to anatomical features and/or anatomical deformities; (3) the ability to reduce or prevent cross-contamination; (4) the ability to reduce tension on tissues at a retracted surgical site; and (5) the ability to provide reduced incision lengths at a surgical site.

Many surgical retractors are not designed for specific surgical procedures and do not consider the anatomy of the patient at a particular surgical site. If surgical retractor is not ergonomically designed for a specific procedure and tissue anatomy (e.g., specific muscle(s), muscle groups, and other tissues), the risk of damage to these tissues may increase. General surgical retractors are typically utilized to perform specific surgical procedures where no ergonomically designed surgical retractor design is available to the surgeon. For example, a vaginal, anal, or rectal speculum has traditionally been utilized during surgical procedures that lengthen the gastrocnemius and/or soleus muscles.

SUMMARY

The various devices, systems, and methods of the present disclosure have been developed in response to the present state of the art, and in particular, in response to the problems and needs in the art that have not yet been fully solved by currently available technology. The present disclosure describes anatomically correct (i.e. fit-for-purpose) surgical retractors and methods for retracting tissue, such as, but not limited to, the lower extremity, upper extremity, abdominal, rectal and other areas of the body during a surgical procedure.

In some embodiments, a surgical retractor for retracting one or more tissues may include a first handle and a second handle. The surgical retractor may also include a first blade, with proximal and distal ends, that is coupled to the first handle, and a second blade, with proximal and distal ends, that is coupled to the second handle. The surgical retractor may also include a hinge that is configured to pivotally couple the distal end of the first blade to the distal end of the second blade.

In other embodiments, a surgical retractor for retracting one or more tissues may include a first blade with proximal and distal ends, and a second blade with proximal and distal ends. The distal end of the first blade may be pivotally coupled to the distal end of the second blade. The surgical retractor may also include a ratcheting mechanism that is configured to maintain a selected distance between the proximal end of the first blade and the proximal end of the second blade.

In yet other embodiments, a method for retracting tissue may utilize a surgical retractor that includes a first handle, a second handle, a first blade with proximal and distal ends coupled to the first handle, and a second blade with proximal and distal ends coupled to the second handle. The method may also include inserting the surgical retractor between a first tissue and a second tissue and pivoting the proximal ends of the first and second blades away from each other about a pivot point positioned proximate the distal ends of the first and second blades to retract the first and second tissues away from each other.

Although the present surgical retractor is particularly designed for use in the lower extremities, the present surgical retractor may also be used in any areas of the body including, but not limited to: the upper extremities, the abdominal area, the rectal area, etc., where anatomically curved blades as described herein may be beneficial.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

Figure 1:
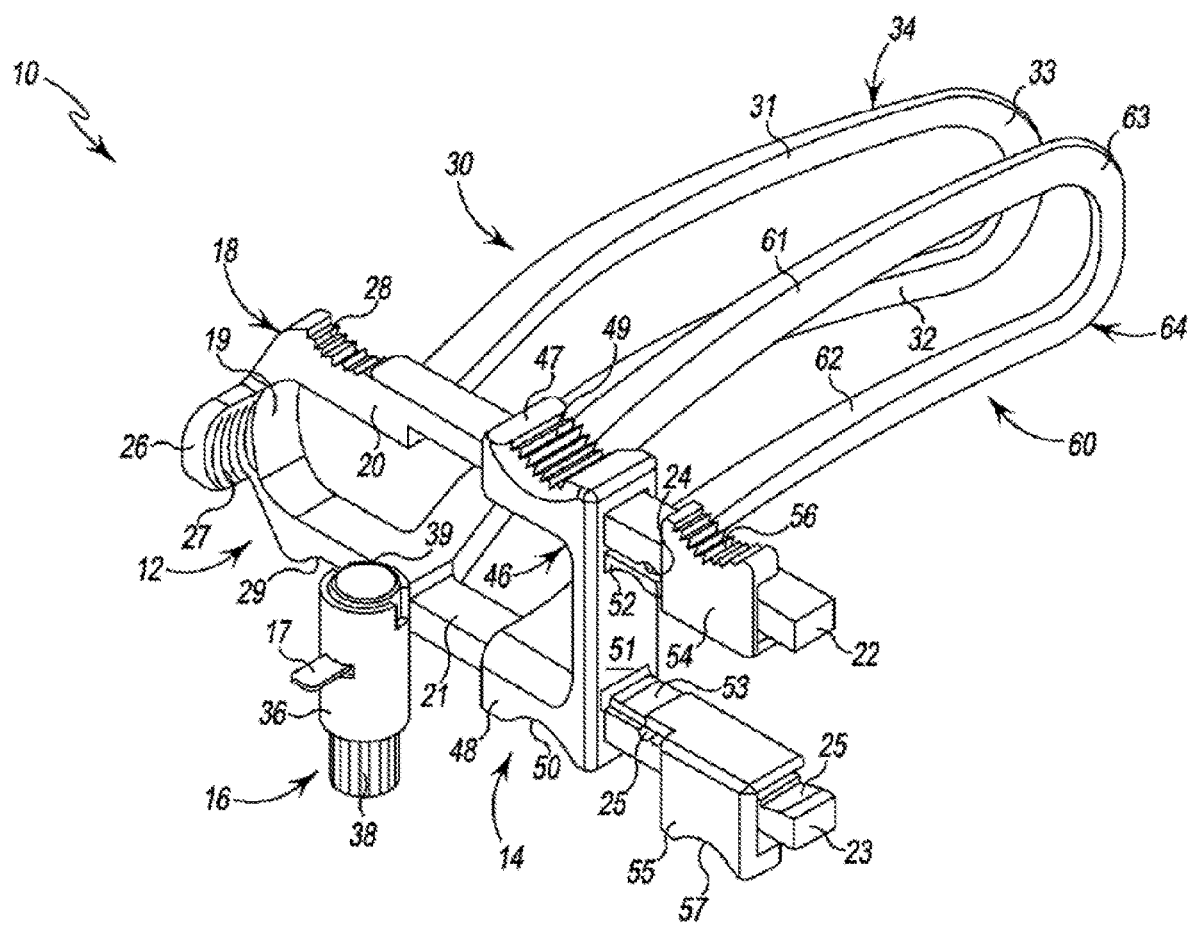
FIG. 1 is an isometric view of a surgical retractor fashioned in accordance with the present principles.
Figure 2:
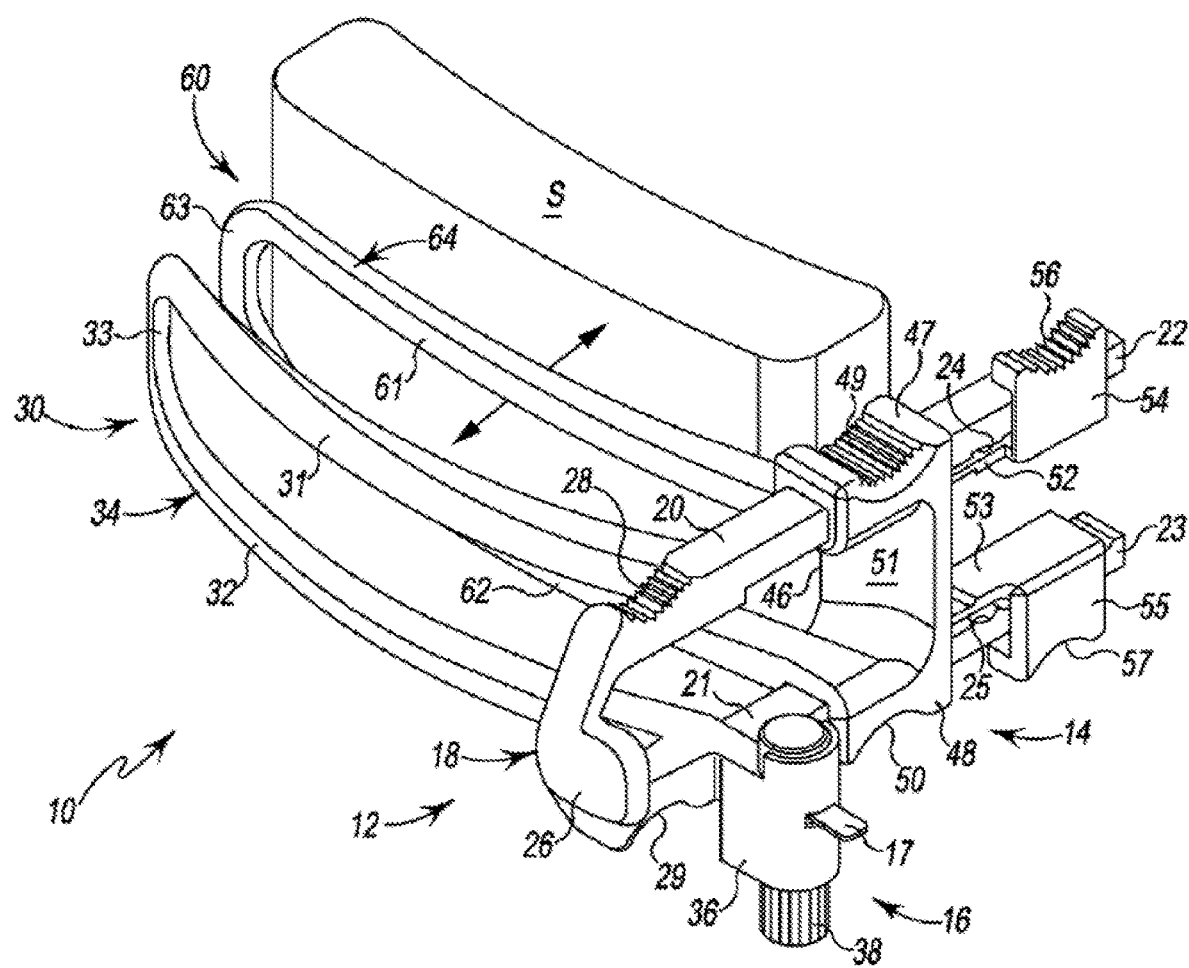
FIG. 2 is another isometric view of the surgical retractor of FIG. 1 shown in conjunction with a soleus muscle.

It is to be understood that the drawings are for purposes of illustrating the concepts of the disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the devices, instruments, systems, and methods, as represented in the Figures, is not intended to limit the scope of the present disclosure, as claimed, but is merely representative of exemplary embodiments of the present disclosure.

The surgical retractors described herein may be ergonomically designed to make it easy to maneuver and use these surgical retractors in both adult and pediatric patients. These surgical retractors are preferably, but not necessarily, designed for single use in order to reduce the risk of cross-contamination. Accordingly, these surgical retractors may be pre-sterilized and pre-packaged in sterile packaging in order to reduce set-up time, cleaning costs, and the risk of infection. However, it will also be understood that in other embodiments the surgical retractors described herein may be re-sterilized and re-used multiple times.

FIGS. 1-11 illustrate one embodiment of a surgical retractor 10 for retracting tissue, such as muscles, during a surgical procedure. The surgical retractor 10 is preferably, but not necessarily, designed for one time use and may be disposable. In a multiple use form, the surgical retractor 10 may be made from a suitable metal, metal alloy, or other material that allows the surgical retractor 10 to be used multiple times and/or be cleaned and/or sterilized as necessary. The surgical retractor 10, with the exception of various components associated with light assembly 16 of the surgical retractor 10, is thus also preferably, but not necessarily, made from one or more appropriate plastics such as are known in the art. However, other suitable materials such as metal may be used. The surgical retractor 10 may be used in lower extremity, upper extremity, abdominal, rectal and other areas of the body during a surgical procedure, particularly, but not necessarily, for retraction of muscles during a surgical procedure.

Continuing with FIGS. 1-11, the surgical retractor 10 is shown in several of these Figures with respect to the gastrocnemius muscle G and the soleus muscle S of the body, it being appreciated that such is only illustrative, and not restrictive, of use of the surgical retractor 10 for any particular tissue, muscle, muscles, muscle groups. One exemplary surgical procedure that may utilize the surgical retractors 10, 100 described herein for the gastrocnemius muscle G and/or the soleus muscle S is a Baumann procedure where the surgical retractor is inserted between the gastrocnemius muscle G and the soleus muscle S. In particular, a Baumann procedure consists of intramuscular lengthening (recession) of the gastrocnemius muscle in the deep interval between the soleus and gastrocnemius muscles. The goal of the procedure is to increase ankle dorsiflexion when ankle movement is restricted by a contracted gastrocnemius muscle. Unlike a Vulpius procedure, which only lengthens the superficial gastrocnemius aponeurosis, the Baumann procedure can do an isolated lengthening of the deep gastrocnemius aponeurosis, but which may also lengthen the superficial soleus aponeurosis. Another procedure is the Strayer procedure which is a posteromedial surgical treatment option for clinically relevant gastrocnemius equinus contracture. Identifying and protecting the sural nerve is an important component of the procedure.

The surgical retractors 10, 100 described herein may further be used to lengthen the plantaris tendon to treat ankle equinus or muscular contracture, or as a supplementary treatment of plantar fasciitis, hallux valgus, symptomatic adult acquired flatfoot, metatarsalgia, and/or diabetic foot ulcers, it being appreciated that the aforementioned surgical procedures are only illustrative, and not restrictive, of use of the surgical retractors 10, 100 for any particular surgical procedure or tissue.

Continuing with FIGS. 1-11, the surgical retractor 10 has a first retraction arm 12, a second retraction arm 14 (the nomenclature first and second being arbitrary), and a light assembly 16, the light assembly 16 may be carried on the first retraction arm 12, while the second retraction arm 14 is supported on and movable with respect to the first retraction arm 12. It should be appreciated that other configurations are contemplated.

The first retraction arm 12 is characterized by an elongated U-shaped body 18 defining an arced or curved end segment 19, a first tine 20 extending from a first end of the arced end segment 19, and a second tine 21 extending from a second end of the arced end segment 19. A tab 26 or flange extends from a side of the arced end segment 19 in order to provide a place for a user to hold and/or push against the frame, particularly, but not necessarily, during positioning of the surgical retractor 10. As such, an inner surface 27 of the tab 26 is preferably, but not necessarily, ribbed or otherwise textured. Of course, other manners of providing a finger or hand grip may be used and are contemplated.

The first retraction arm 12 has a first blade 30 that extends outwardly from a side of the first and second tines 20, 21. The first blade 30 is defined by a body 34 that generally forms a loop that extends from a side of the first tine 20 to a same side of the second tine 21, and defining an elongated "U" shape with an open interior. Particularly, the body 34 has an upper leg 31 that extends from the side of the first tine 20 to an arched end 33, and a lower leg 32 that extends from the side of the second tine 21 to the arched end 33. The body 34 defines a blade that is generally transverse to the first and second tines 20, 21 but which preferably, but not necessarily, includes a curvature or bow (see additionally FIGS. 10-11) in order to be anatomically correct with respect to the muscle (tissue) that the blade 30 will contact. As such, and in keeping with the surgical retractor 10 embodied as a gastrocnemius muscle G/soleus muscle S retractor, the blade 30 is curved in like manner as the gastrocnemius muscle G. The blade 30 may be made with other curvature(s) or no curvature depending on the muscle(s) or muscle group(s) being retracted. In this manner, the surgical retractors 10, 100 may be anatomically designed such that the surgical retractor 10 is fit for a particular purpose and/or surgical procedure.

A depression 28 or notch is provided in the upper surface of the first tine 20 proximate the arced end segment 19. The depression 28 preferably, but not necessarily, includes serrations or the like to provide a gripping area. Likewise, a depression or notch 29 is provided in the lower surface of the second tine 21 proximate the arced end segment 19. The depression 29 preferably, but not necessarily, includes serrations or the like to provide a gripping area. The serrated depressions 28 and 29 allow a user to easily grasp or hold the first retraction arm 12 during use.

Figure 9:
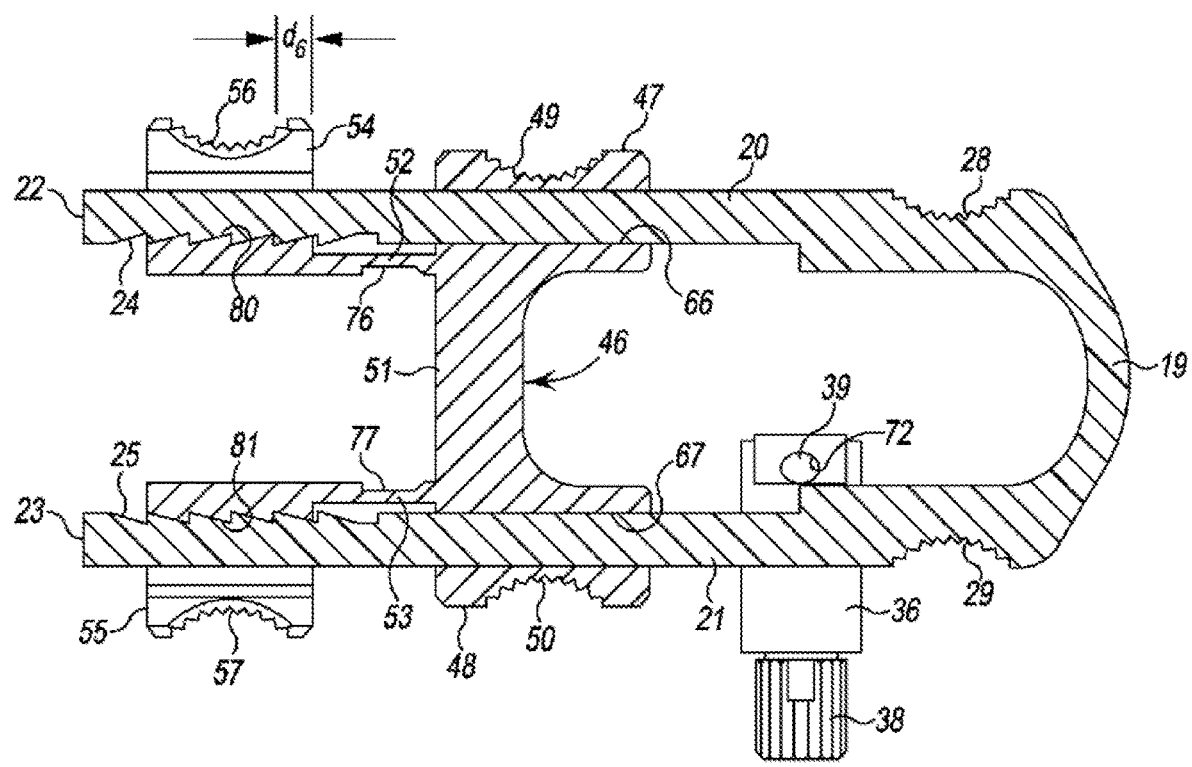
FIG. 9 is a sectional view of the surgical retractor of FIG. 8 taken along line 9-9 thereof.

As best seen in FIG. 9, an end 22 of the first tine 20 includes teeth, serrations 24 or the like on a lower surface thereof, while an end 23 of the second tine 21 includes teeth, serrations 25 or the like on an upper surface thereof, each forming a part of a ratchet or ratcheting mechanism that provides controlled movement and positional holding of the second retraction arm 14 relative to the first retraction arm 12. The interaction of the second retraction arm 14 relative to the first retraction arm 12 is discussed below.

The second retraction arm 14 is characterized by a carriage 46 defined by a generally U-shaped body 51 having an upper limb 47 and a lower limb 48. A depression 49 or notch is provided in the upper surface of the upper limb 47, the depression 49 preferably, but not necessarily, including serrations or the like to provide a gripping area. Likewise, a depression 50 or notch is provided in the lower surface of the lower limb 48, the depression 50 preferably, but not necessarily, including serrations or the like to provide a gripping area. The serrated depressions 49, 50 allow a user to easily grasp or hold the carriage 46 during use.

The carriage 46 is movably supported on and by the first and second tines 20, 21 of the first retraction arm 12. Particularly, the upper limb 47 of the carriage body 51 has a bore 66 (see, e.g., FIGS. 7 and 9) that is shaped complementary to the shape of the first tine 20 such that the first tine 20 extends through the bore 66. The lower limb 48 of the carriage body 51 has a bore 67 (see, e.g., FIGS. 7 and 9) that is shaped complementary to the shape of the second tine 21 such that the second tine 21 extends through the bore 67. The carriage 46 thus slides or moves along the first and second tines 20, 21. Such movement is controlled by upper and lower ratchet/ratcheting mechanisms between the first retraction arm 12 and the second retraction arm 14. As indicated above, the first tine 20 has a first ratchet portion of the upper ratchet/ratcheting mechanism that include serrations along the lower surface of the end 22 of the first tine 20, while the second tine 21 has a first ratchet portion of the lower ratchet/ratcheting mechanism that include serrations along the upper surface of the end 23 of the second tine 21.

A second ratchet portion of the upper ratchet/ratcheting mechanism includes an upper, resilient finger 52 that extends from the end of the body 51 of the carriage 46 with an actuator 54 situated on the end of the resilient finger 52, the actuator 54 at least partially surrounding the end 22 of the first tine 20. The actuator 54 has a serrated notch 56 that provides an area to be grasped by a user's finger. As best seen in FIG. 9, the finger 52 is resilient through a reduced thickness portion 76 of the finger 52 allowing for flexibility and spring action of the finger 52, and thus the actuator 54 relative to the first tine 20. The actuator 54 has serrations 80 that face and mesh with the serrations 24 of the first tine 20. The finger 52 and the actuator 54 are normally biased in a latched position as shown in FIG. 9. Depressing the actuator 54 disengages the actuator serrations 80 from the serrations 24 of the first tine 20 to allow movement of the actuator 54 and thus the upper limb 47 of the carriage body 51.

A second ratchet portion of the lower ratchet/ratcheting mechanism includes a lower, resilient finger 53 that extends from the end of the body 51 of the carriage 46 with an actuator 55 situated on the end of the resilient finger 53, the actuator 55 at least partially surrounding the end 23 of the second tine 21. The actuator 55 has a serrated notch 57 that provides an area to be grasped by a user's finger. As best seen in FIG. 9, the finger 53 is resilient through a reduced thickness portion 77 of the finger 53 allowing for flexibility and spring action of the finger 53 and thus the actuator 55 relative to the second tine 21. The actuator 55 has serrations 81 that face and mesh with the serrations 25 of the second tine 21. The finger 53 and the actuator 55 are normally biased in a latched position as shown in FIG. 9. Depressing the actuator 55 disengages the actuator serrations 81 from the serrations 25 of the second tine 21 to allow movement of the actuator 55 and thus the lower limb 48 of the carriage body 51.

Figure 3:
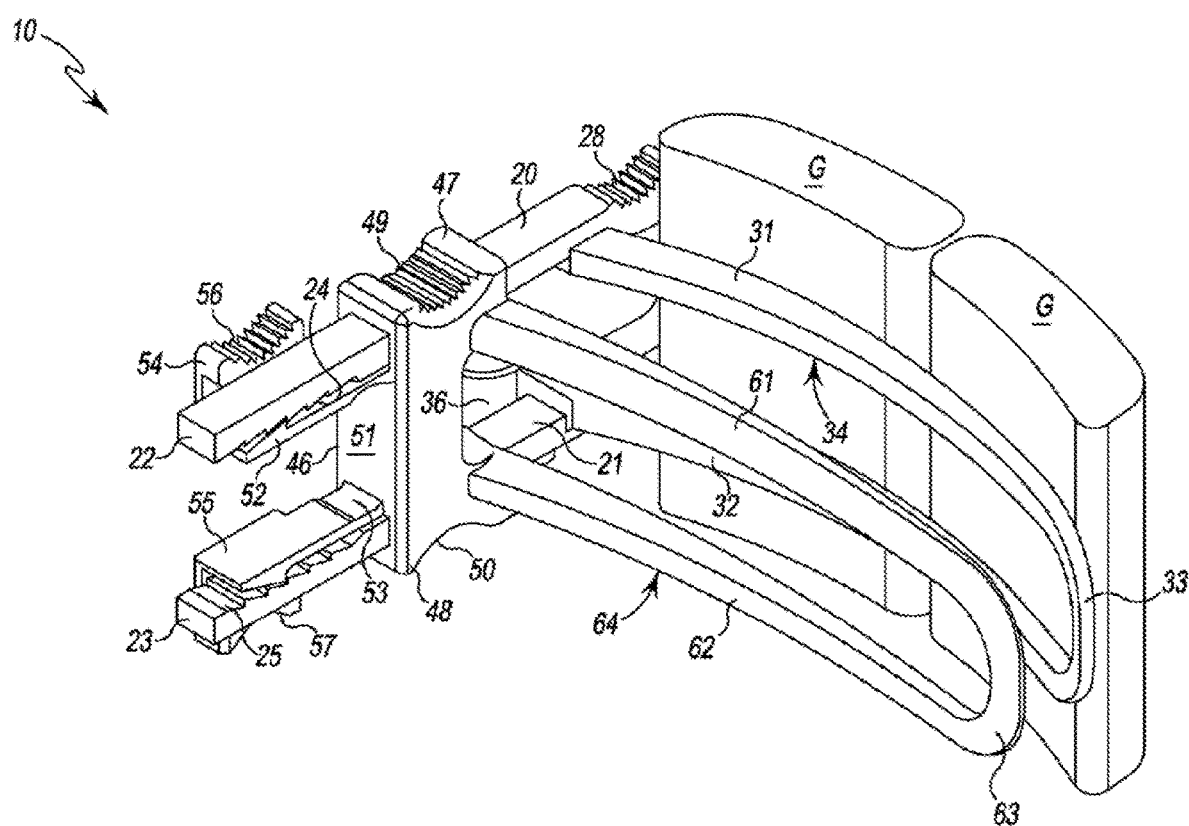
FIG. 3 is another isometric view of the surgical retractor of FIG. 1 shown in conjunction with a gastrocnemius muscle.

As best seen in FIG. 3, the second retraction arm 14 has a second blade 60 that extends outwardly from a side of the carriage 46. The second blade 60 is defined by a body 64 that generally forms a loop that extends from a side of the upper limb 47 of the carriage body 51 to a same side of the lower limb 48 of the carriage body 51, and defining an elongated "U" shape with an open interior. Particularly, the body 64 has an upper leg 61 that extends from the side of the upper limb 47 of the carriage body 51 to an arched end 63, and a lower leg 62 that extends from the side of the lower limb 48 of the carriage body 51 to the arched end 63. The body 64 defines a blade that is generally transverse to the carriage body 51 and the first and second tines 20, 21 but which preferably, but not necessarily, includes a curvature or bow (see additionally FIGS. 10-11) in order to be anatomically correct with respect to the muscle (tissue) that the blade 60 will contact. As such, and in keeping with the surgical retractor 10 embodied as a gastrocnemius muscle G/soleus muscle S retractor, the blade 60 is curved in like manner as the soleus muscle S. The blade 60 may be made with other curvature(s) or no curvature depending on the muscle(s) or muscle group(s) being retracted. In this manner, the surgical retractors 10, 100 described herein may be anatomically designed such that these surgical retractors 10, 100 may fit a particular purpose and/or surgical procedure.

The carriage 46 and thus the blade 60 (the second retraction arm 14) is movable (adjustable) along the first and second tines 20, 21 of the first retraction arm 12. The carriage 46 moves freely in the retracting/opening direction (i.e. away from the second blade 30) by free ratcheting of the upper and lower ratchet mechanisms through spring action of actuators 54, 55. Movement in the un-retracting/closing direction (i.e. towards the second blade 30) however, requires manual actuation by depressing both actuators 54 and 55 to overcome the spring bias of the upper and lower ratchet mechanisms thereby releasing the ratchets and allow sliding movement of the carriage 46. Such movement is indicated by the two oppositely pointing arrows in FIGS. 2 and 5.

Figure 10:
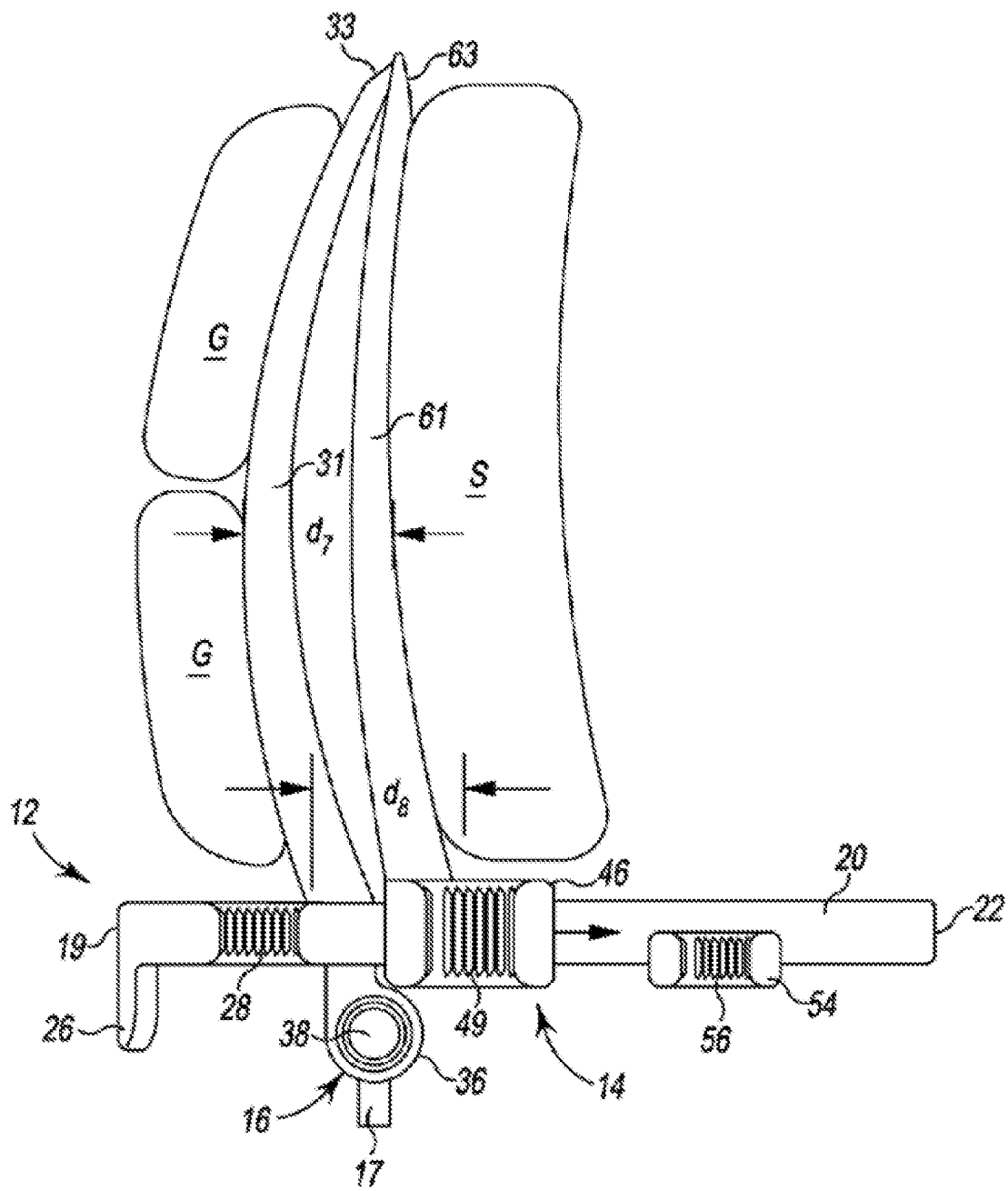
FIG. 10 is a top view of the surgical retractor of FIG. 1 relative to a soleus muscle and a gastrocnemius muscle, with the surgical retractor in an un-retracted position.
Figure 11:
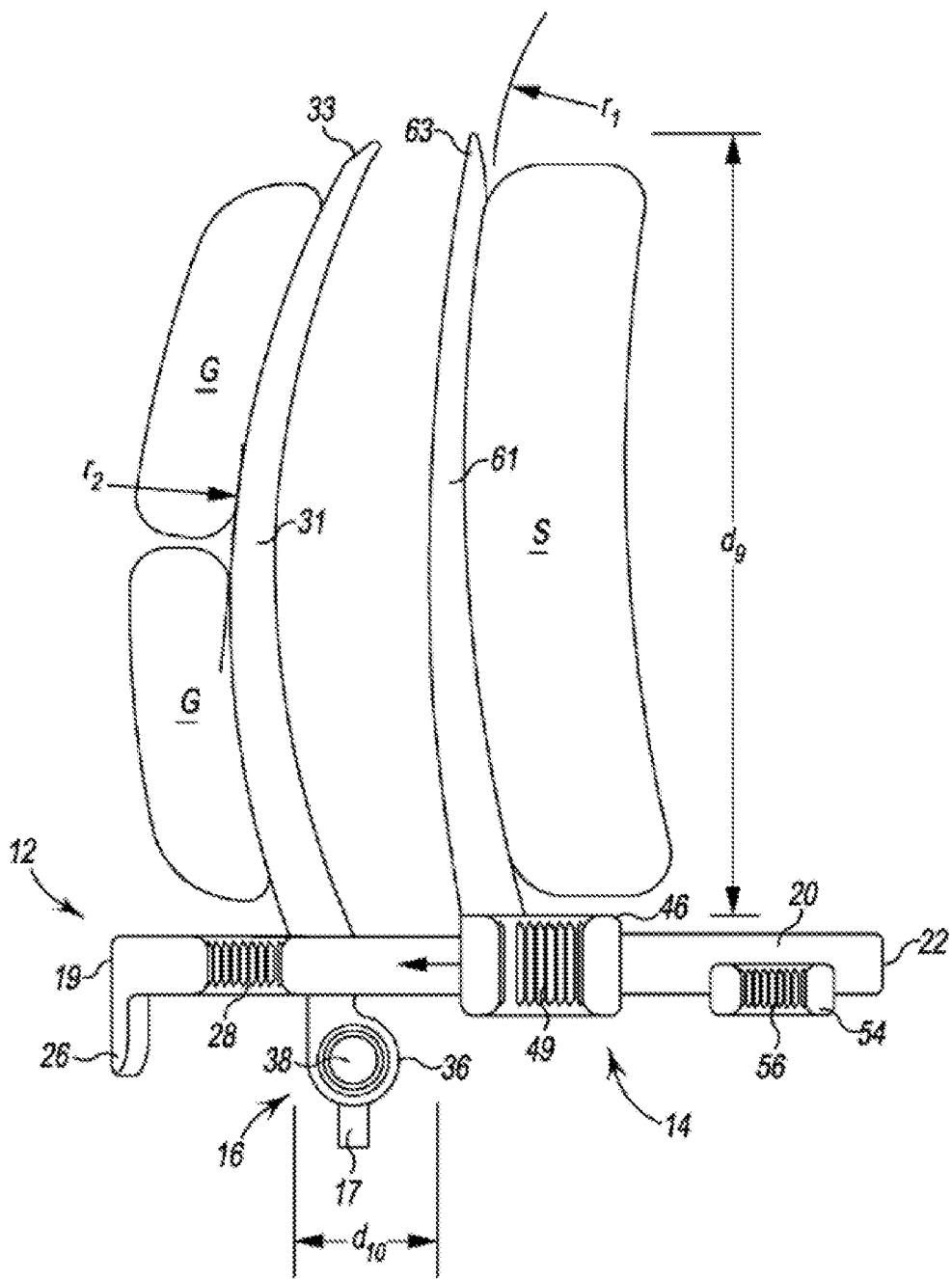
FIG. 11 is a top view of the surgical retractor as shown in FIG. 10 with the surgical retractor in a retracted position.

In FIG. 10, the surgical retractor 10 is in a fully un-retracted position as represented by the arrow extending from the left side of the carriage 46 towards the end 22 of the first tine 20 indicating that the carriage 46 and thus the blade 60 is movable away from the blade 30 to provide tissue retraction. In this position, the blade 60 is closest to the blade 30 and, in particular, the arched end 63 of the blade body 64 of the blade 60 abuts the arched end 33 of the blade body 34 of the blade 30. In FIG. 11, the surgical retractor 10 is in a retracted position as represented by the arrow extending from the right side of the carriage 46 towards the arced end segment 19 of the body 18 of the first retraction arm 12 indicating that the carriage 46 and thus the blade 60 is movable towards the blade 30 to assume an un-retracted position. In this position, the blade 60 is located at some distance away from the blade 30.

Figure 5:
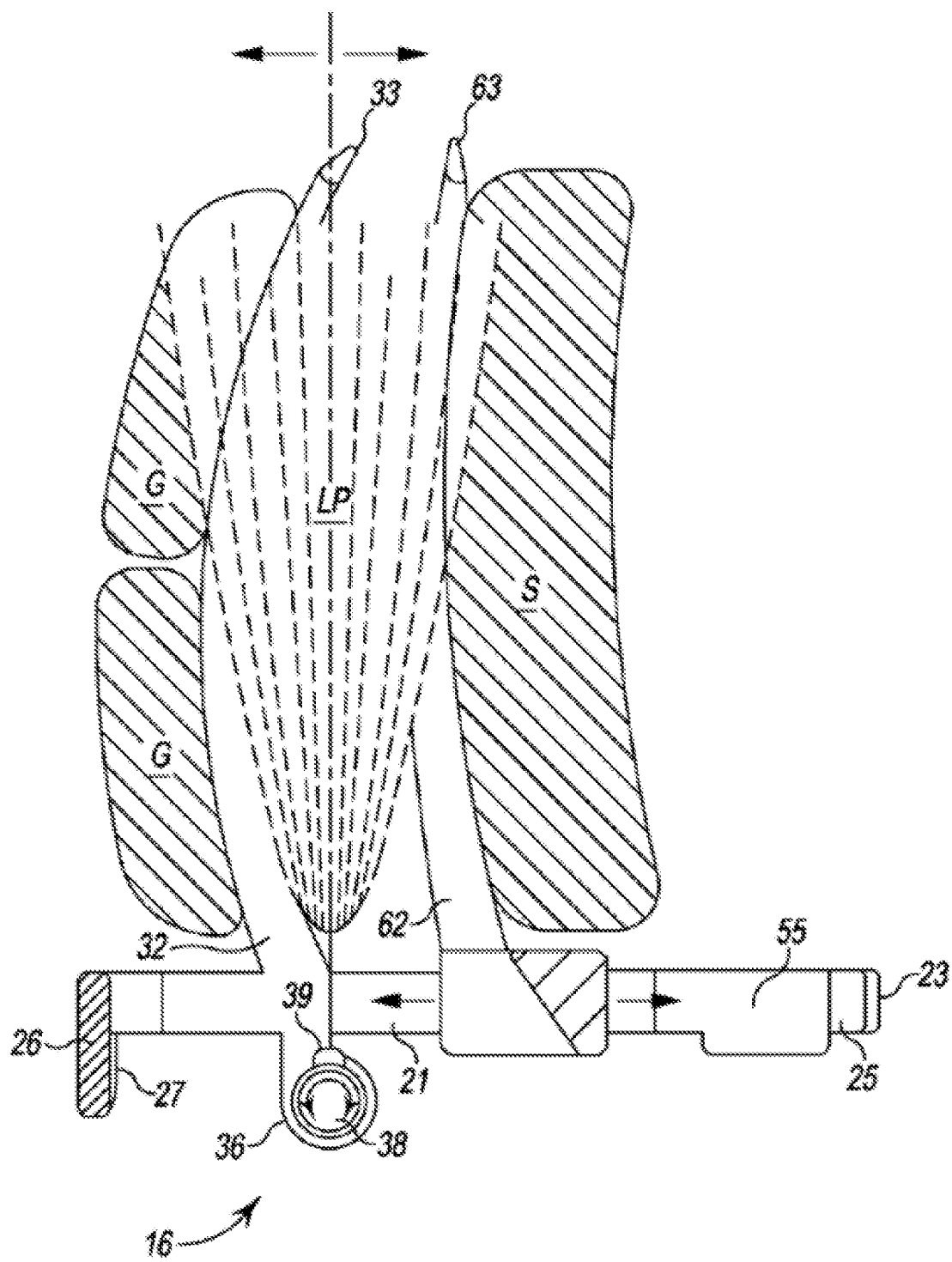
FIG. 5 is a view of the surgical retractor of FIG. 4 taken along line 5-5 thereof showing a light beam pattern from the light of the surgical retractor relative to retraction arms of the surgical retractor and to exemplary muscles being held by the retraction arms.
Figure 6:
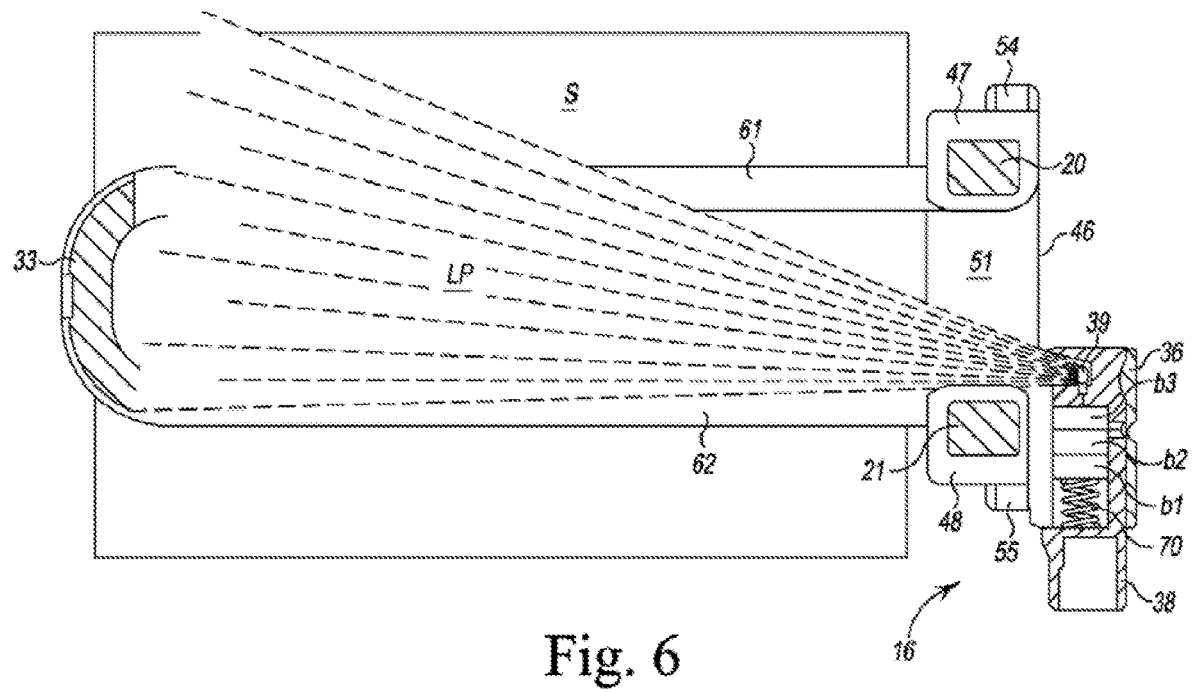
FIG. 6 is a sectional view of the surgical retractor of FIG. 4 taken along line 6-6 thereof showing the light beam pattern from the surgical retractor light.

The light assembly 16 is carried on the first retraction arm 12. With reference to FIG. 6 the light assembly 16 is shown as having a generally cylindrical housing 36 that is situated on a side of the second tine 21 generally opposite the first blade 30. The housing 36 may take forms other than cylindrical, as well as be positioned at different locations on and along the surgical retractor 10. In this form, and as best seen in FIG. 5, the housing 36 is situated opposite to where the lower leg 32 of the blade 30 joins the second tine 21. A light module 38 or assembly is releasably retained in the housing 36. A retention flange 41 helps retain the light module 38 in the housing 36. Particularly, the retention flange 41 is a small finger that protrudes out of the side of the light module 38 that will depress inwardly as it is pushed through the housing 36. Once completely through the housing 36, the flange 41 springs outwardly to lock the light module 38 in the housing 36. The light module 38 includes a light source, such as LED 39, that is preferably, but not necessarily, a light emitting diode (LED). Other types of light sources may be used and are contemplated. However, an LED generates little heat that could interfere with the surgery and is thus preferred, but other low heat or no heat generating light sources may also be used. The LED 39 is electrically connected to an electrical power source, embodied as three (3) disk style batteries b1, b2, b3 stacked upon one another to provide electrical contact between adjacent batteries. Other manners of providing electrical power may be used as well as other styles and/or numbers of batteries that are used. The batteries b1, b2, b3 are biased against one another for electrical contact via an electrically conducting spring 70 or the like that is, in turn, electrically connected to the LED 39 in order to complete an electrical circuit for turning on the light. An insulator 17 (not shown in FIGS. 5 and 6, as the light module 38 is depicted in FIGS. 5 and 6 in the on mode and therefore shining or projecting a beam of light LP), may be provided that extends from the outside to the inside of the housing 36 and between the two batteries b2 and b3. The insulator 17 creates an open circuit to the light electrical circuit so that the light is normally off. Removal of the insulator 17 by pulling it out of the housing completes the light electrical circuit to turn the light on. This is accomplished during use of the surgical retractor 10. Other manners of interrupting and/or making contact between the batteries and the light source may be employed and are contemplated.

The light module 38 is positionable so as to shine the light beam emanating from the light source of the light module 38 on or at a particular area of the surgical retractor 10 and/or on or at a particular tissue or tissue area. While this may be achieved in various manners, the light module 38 of the surgical retractor 10 is able to rotate relative to the housing 36, as indicated by the two-headed arrow on the top of the light module 38 of FIG. 5, such that the light beam or pattern LP (see FIGS. 5 and 6) can shine upon a particular area of the surgical retractor 10 and thus a particular area of a muscle G, S, blade 30, 60 or incision (as indicated by the two, oppositely pointing arrows at the top of the light beam LP of FIG. 5). Rotation of the light module 38 is accomplished by grasping the lower portion (essentially forming a knob) of the light module 38 that extends from the housing 36 and turning as desired.

Another or additional manner of achieving light beam positioning is to allow the light module 38, an equivalent thereof that holds the light source, or the light source itself, to move, slide or otherwise shift position along the surgical retractor 10 or a portion thereof. The light source may also move up or down, or angularly, or otherwise, to position the light beam in any position or orientation.

Various Figures include lines and arrows delineating dimensions, component/part tolerances, or other features and/or aspects regarding one form of the surgical retractor 10. It should be appreciated that these dimensions, component/part tolerances, or other features (e.g. specification of the surgical retractor) are exemplary and can change as necessary. For example, forms of the surgical retractor 10 for muscles or tissues other than the gastrocnemius and soleus may necessitate a change in specification.

Figure 4:
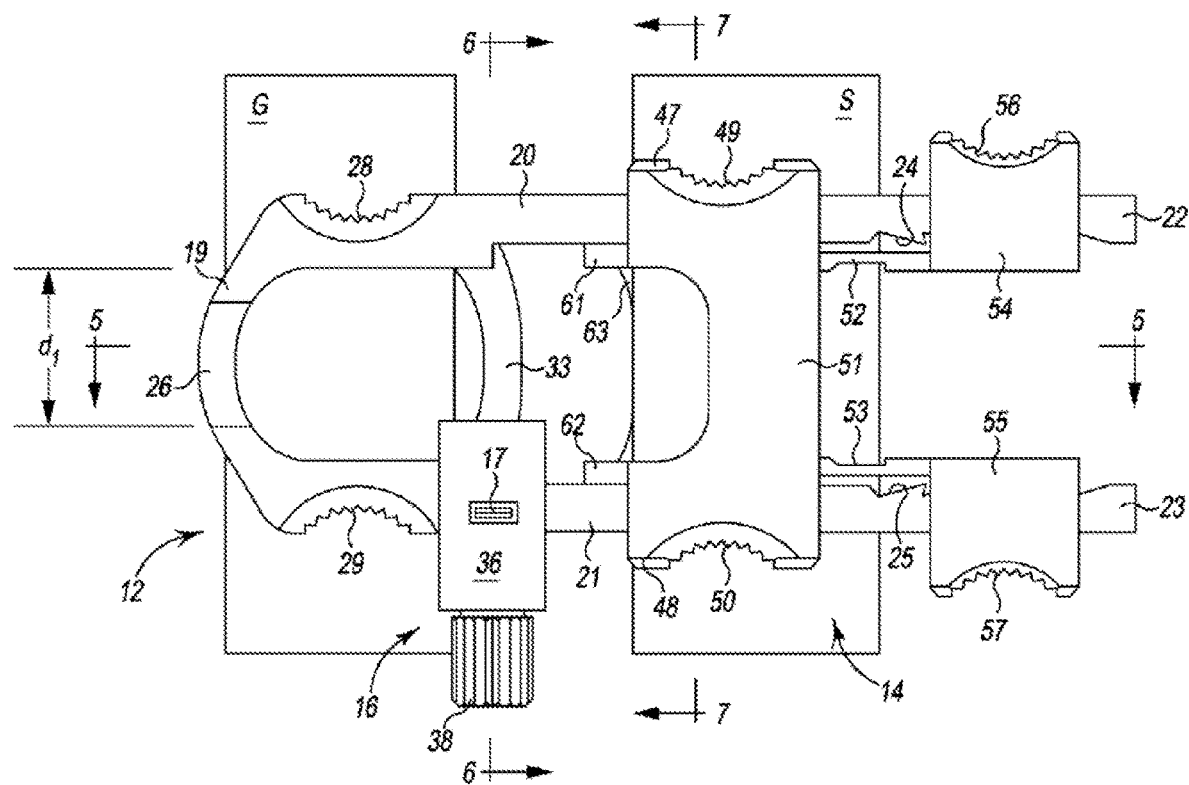
FIG. 4 is a side view of the surgical retractor of FIG. 1 shown in conjunction with both a soleus muscle and a gastrocnemius muscle.
Figure 7:
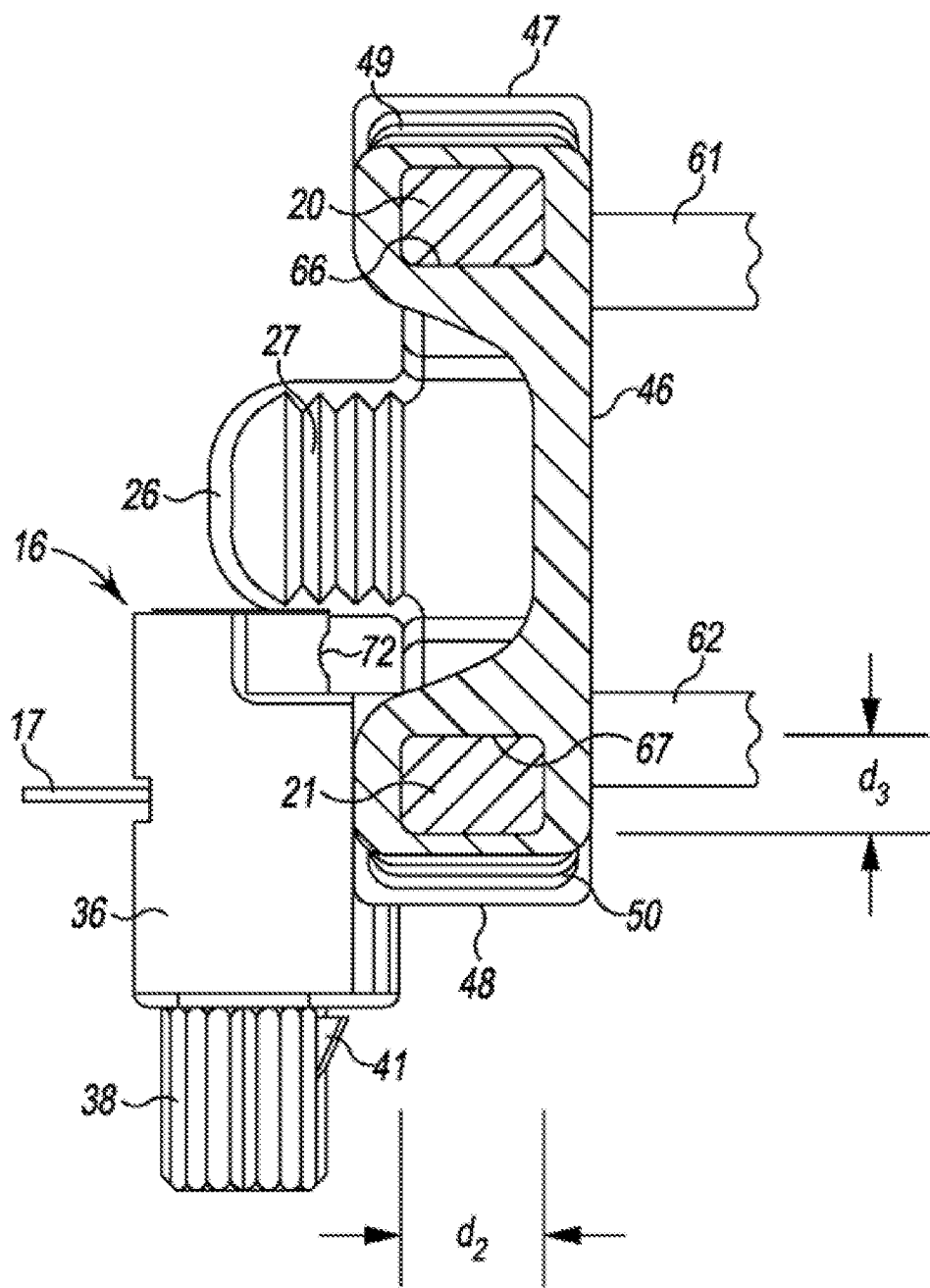
FIG. 7 is a sectional view of the surgical retractor of FIG. 4 taken along line 7-7 thereof.
Figure 8:
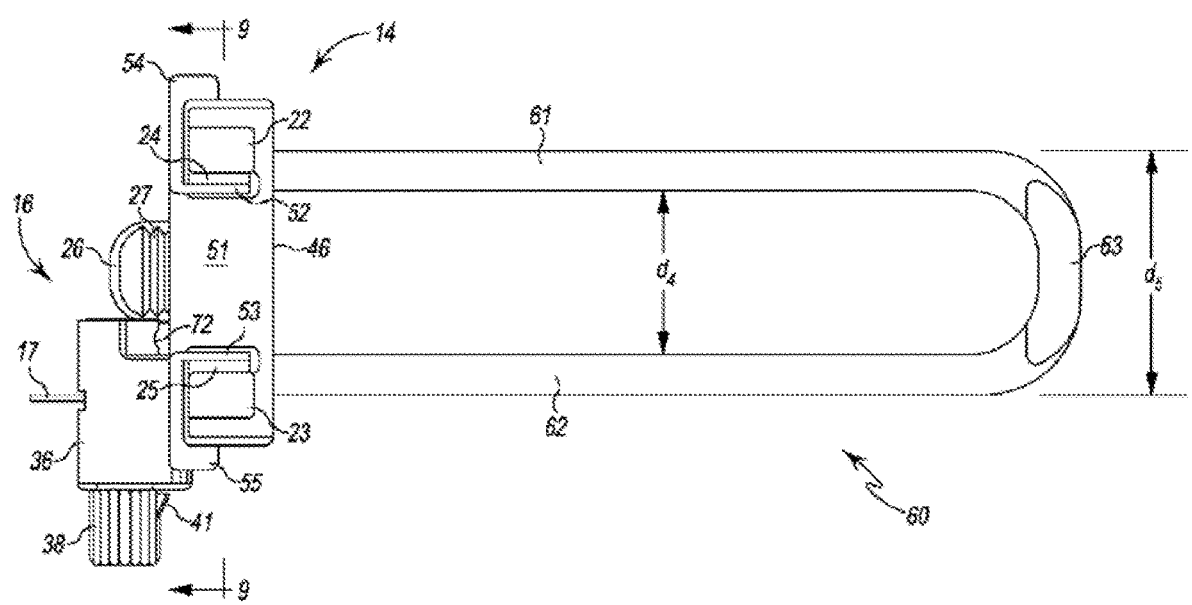
FIG. 8 is a side view of the surgical retractor of FIG. 1.

In FIG. 4, dimension $d_1$ corresponding to 0.784 inches (19.91 millimeters) is given for the distance between the top of the light module 38 housing and the bottom of the first tine 20. In FIG. 7, dimension $d_2$ corresponding to 0.375 inches (9.53 millimeters) is given for the width of the second tine 21 (and of the first tine 20), while dimension $d_3$ corresponding to 0.250 (6.35 millimeters) is given for the height of the second tine 21 (and of the first tine 20). In FIG. 8, dimension $d_4$ corresponding to 1.0 inches (25.4 millimeters) is given for the distance between the bottom of the upper leg 61 and the top of the lower leg 62 of the blade 60, while dimension $d_5$ corresponding to 1.50 inches (38.1 millimeters) is given for the distance between the top of the upper leg 61 and the bottom of the lower leg 62 of the blade 60. In FIG. 9, dimension $d_6$ corresponding to 0.200 inches (5.08 millimeters) is given for the ratchet pitch for the serrations 24 of the first tine 20 and the serrations 80 of the finger 52 forming an upper ratchet mechanism, and for the serrations 25 of the second tine 21 and the serrations 81 of the finger 53 forming a lower ratchet mechanism.

In FIG. 10, dimension $d_7$ corresponding to 0.911 inches (23.13 millimeters) is given for the width of the blades 30 and 60 at a line between the two arrows illustrating incision insertion width when the surgical retractor 10 is in the closed position, while dimension $d_8$ corresponding to 0.931 inches (23.64 millimeters) is the width of the blades 30 and 60 at a line between the two arrows illustrating maximum retraction width when the surgical retractor 10 is in the closed position. In FIG. 11, dimension $d_9$ corresponding to 4.906 inches (124.62 millimeters) is given for the length of the blade 60, and a radius $r_1$ corresponding to 11.394 inches (289.42 millimeters) is given for the radius of curvature of the blade 60, dimension $d_{10}$ corresponding to 1.50 inches (38 millimeters) is given for the distance or length of retraction of the blade 60 relative to the blade 30 (tissue), and a radius $r_2$ corresponding to 5.89 inches (149.6 millimeters) is given for the radius of curvature of the blade 30.

The surgical retractor 10 is preferably, but not necessarily, ergonomically designed so that it can be inserted into a patient's incision by utilizing one's left or right hand. Particularly, when the surgical retractor 10 is in the closed or un-retracted position, the blades 30 and 60 are inserted into the incision. After insertion of the blades 30, 60, the grooved tab 26 of the first retractor arm 12 is manipulated by the thumb while the second retractor portion 14 is grasped by the other hand. The surgical retractor 10 is manually retracted by the user to move the blade 60 away from the blade 30 to create a gap between the blades 30 and 60 for scalpel clearance. The upper and lower ratchet mechanisms incrementally ratchet along the first and second tines, preventing back movement of the carriage, and temporarily fixing the position of the carriage, and thus the second blade relative to the first blade. When the actuators 54, 55 are released, the upper and lower ratchet mechanisms will automatically hold the carriage 46 of the second retraction portion 14, the blade 60 of the second retraction portion 14 relative to the first and second tines 20, 21 of the first retraction portion 14, as well as the blade 30 during surgery. The LED is actuated by removing the plastic insulator 17 that protrudes form the side of the housing 36. This may be done before the blades 30, 60 are inserted into the incision. The LED is manipulated as appropriate to shine the light beam onto the desired incision area, muscle (tissue) and/or blade. Manipulation of the LED may be done as much as needed. Manipulation of the actuator 54, 55 releases the associated ratchets to allow the carriage 46 of the second retractor portion 14, and thus the blade 60, to be returned manually to a closed position. Other manners of utilizing the surgical retractor 10 are contemplated and consistent with the present teachings herein.

Figure 12:
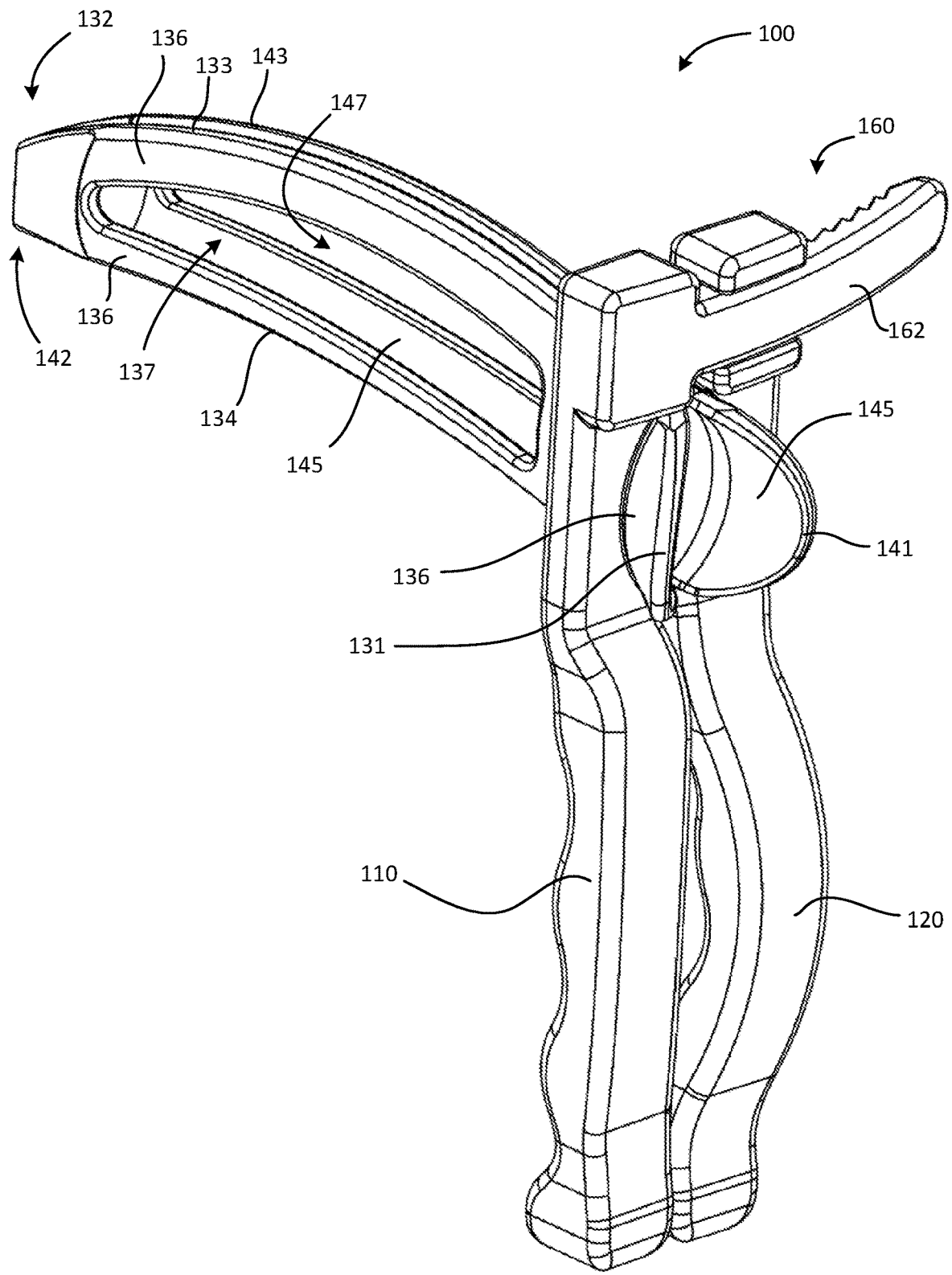
FIG. 12 is a perspective view of a surgical retractor in an un-retracted position, according to another embodiment of the present disclosure.
Figure 13:
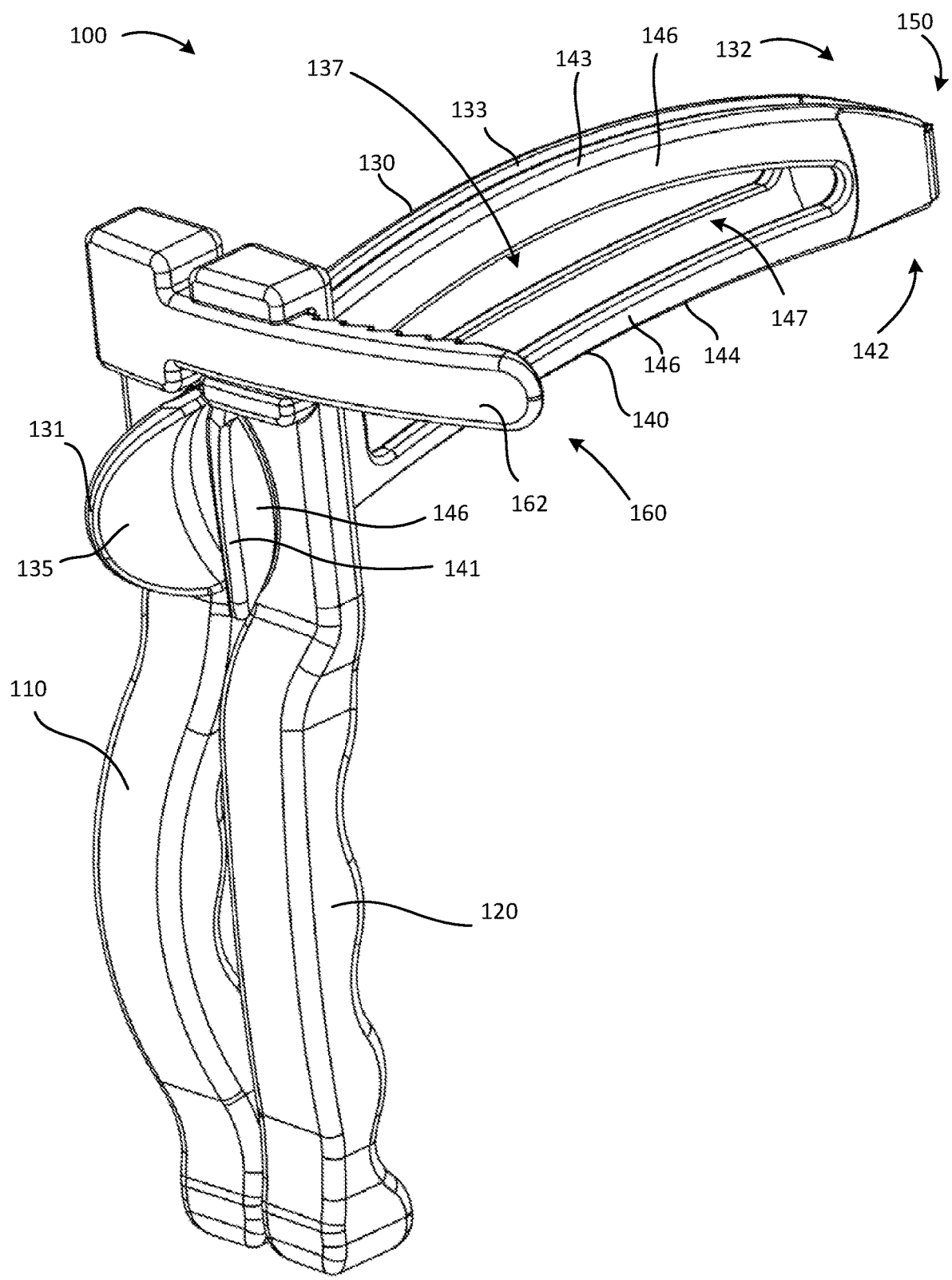
FIG. 13 is another perspective view of the surgical retractor of FIG. 12.
Figure 14:
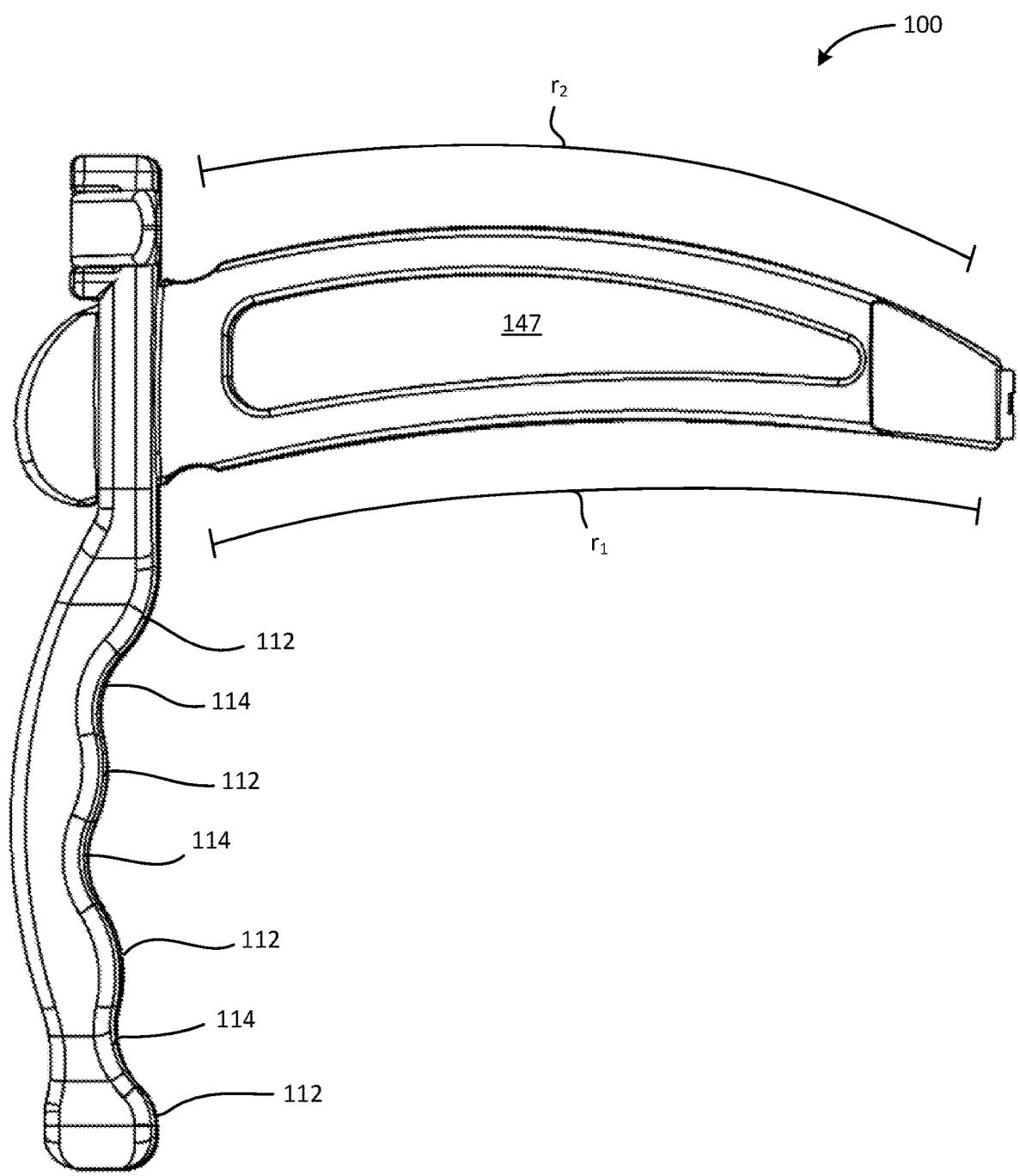
FIG. 14 is a right side view of the surgical retractor of FIG. 12.
Figure 19:
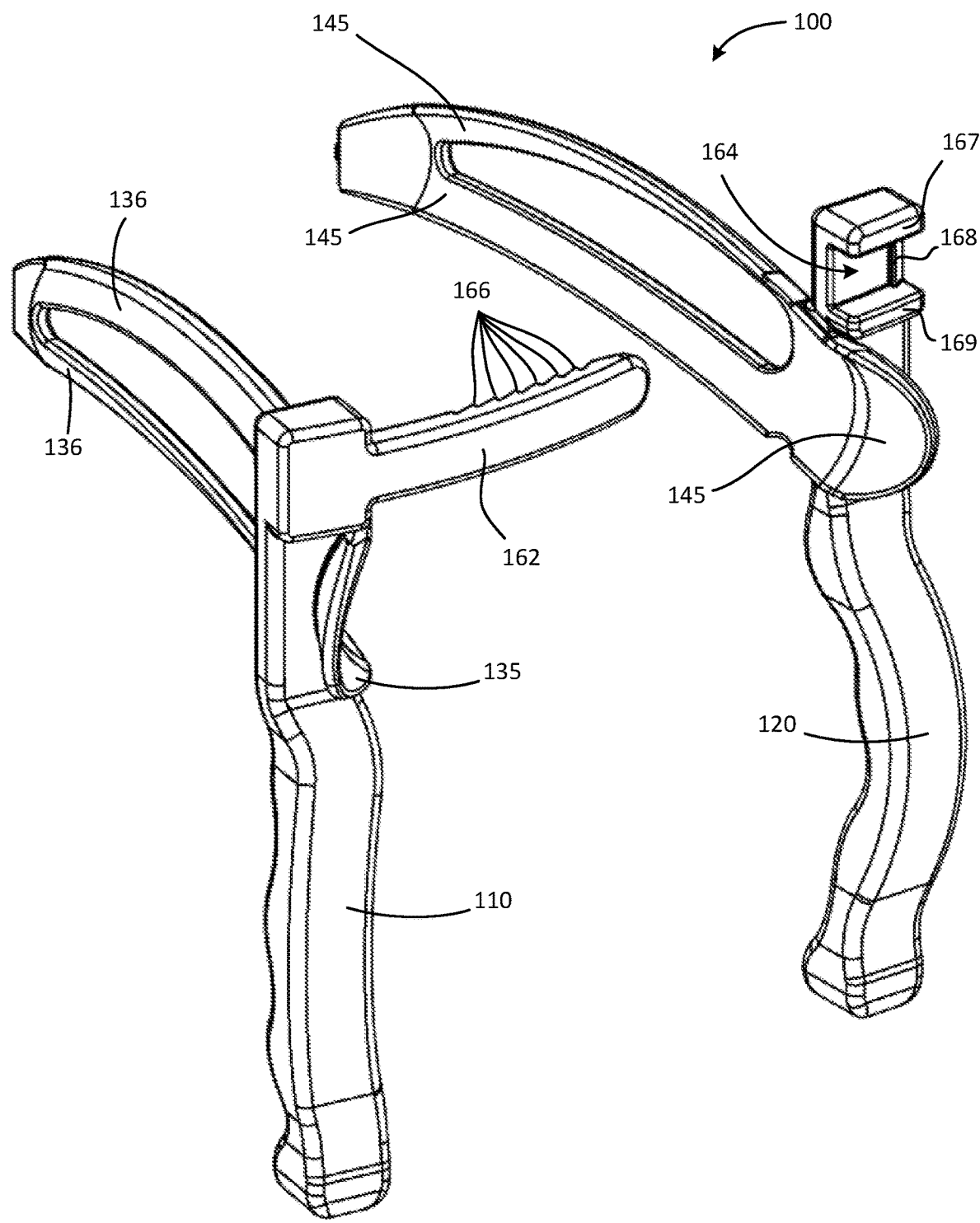
FIG. 19 is an exploded view of the surgical retractor of FIG. 12.
Figure 20:
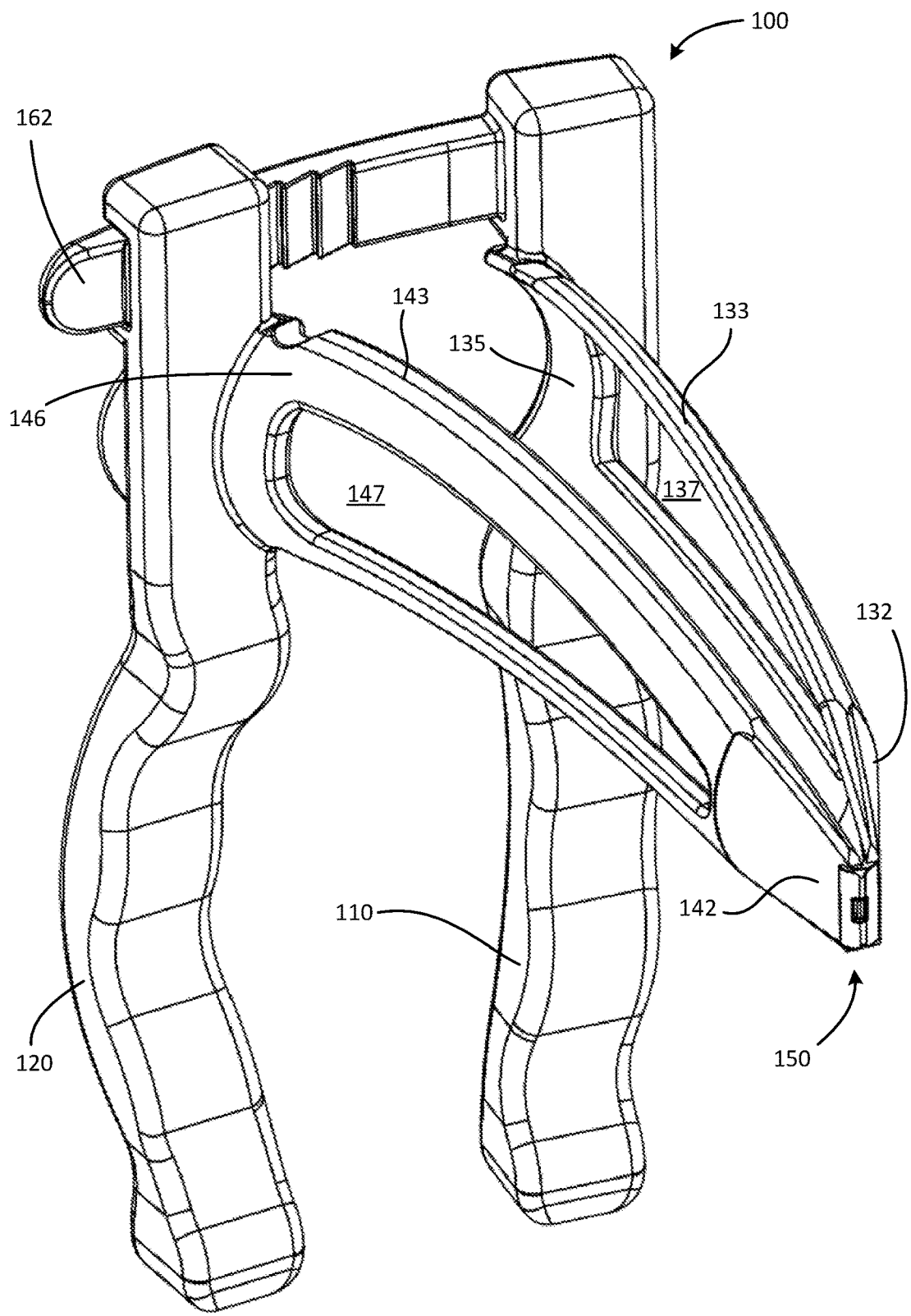
FIG. 20 is a perspective view of the surgical retractor of FIG. 12 in a retracted position.

FIGS. 12-20 illustrate various views of a surgical retractor 100 according to another embodiment of the present disclosure. FIGS. 12, 13, and 20 are perspective views of the surgical retractor in un-retracted and retracted positions; FIG. 14 is a right side view of the surgical retractor 100 in an un-retracted position; FIGS. 15-18 show side views of the proximal and distal ends of the surgical retractor 100, in both the un-retracted and the retracted positions; and FIG. 19 shows an exploded view of the surgical retractor 100. The surgical retractor 100 may generally comprise a first handle 110, a second handle 120, a first blade 130, a second blade 140, a hinge 150, and a ratcheting mechanism 160.

The first and second handles 110, 120 may be ergonomically shaped to conform to a surgeon's hand. For example, the first and second handles 110, 120 may curve away from each other (as best seen in FIGS. 15-18), and/or may curve in the proximal direction toward the surgeon (as best seen in FIG. 14). The first and second handles 110, 120 may also include one or more raised bumps 112 and depressions 114 configured to ergonomically conform to a surgeon's fingers during use of the surgical retractor 100.

The first blade 130 may be coupled to the first handle 110 and the second blade 140 may be coupled to the second handle 120. In at least one embodiment, the first and second blades 130, 140 may be integrally formed with the first and second handles 110, 120. For example, the first and second blades 130, 140 may be integrally formed with the first and second handles 110, 120 via an injection molding process where the surgical retractor 100 is formed from a suitable plastic or metal material (or any other suitable material).

The first blade 130 may have a proximal end 131 (which is typically closer to the surgeon during a surgical procedure), and a distal end 132 (which is typically furthest away from the surgeon during the surgical procedure). The first blade 130 may also include a first blade superior edge 133 that extends from the proximal end 131 of the first blade 130 to the distal end 132 of the first blade 130 along a first superior radius $r_2$ (see FIG. 14), and a first blade inferior edge 134 extending from the proximal end 131 of the first blade 130 to the distal end 132 of the first blade 130 along a first inferior radius $r_1$, as shown in FIG. 14. Likewise, the second blade 140 may have proximal and distal ends 141, 142, a second blade superior edge 143 that extends from the proximal end 141 of the second blade 140 to the distal end 142 of the second blade 140 along a second superior radius $r_2$, and a second blade inferior edge 144 extending from the proximal end 141 of the second blade 140 to the distal end 142 of the second blade 140 along a second inferior radius $r_1$.

In at least one embodiment, the first and second inferior radii $r_1$ of the first and second blades 130, 140 may be greater than the first and second superior radii $r_2$ of the first and second blades 130, 140. In this manner, the first blade superior edge 133 and the first blade inferior edge 134 may approach each other moving from the proximal end 131 of the first blade 130 toward the distal end 132 of the first blade 130. In similar fashion, the second blade superior edge 143 and the second blade inferior edge 144 may approach each other moving from the proximal end 141 of the second blade 140 toward the distal end 142 of the second blade 140. This differential curvature arrangement between the superior and inferior edges of the blades may: (1) provide an anatomic separation between the two retracted tissues; and (2) provide an enlarged working gap area for the surgeon in which to perform surgical procedures within the surgical wound that is retracted by the surgical retractor 100.

In one non-limiting embodiment, the first and second inferior radii $r_1$ may correspond to about 11.394 inches (about 289.4 millimeters) and the first and second superior radii $r_2$ may correspond to about 5.89 inches (about 149.6 millimeters). However, it will be understood that, in other embodiments, any radius size may be used for any of the first and second inferior radii $r_1$ and the first and second superior radii $r_2$ in any order or combination. Moreover, it will also be understood that, in other embodiments, the first and second superior radii $r_2$ of the first and second blades 130, 140 may be greater than the first and second inferior radii $r_1$ of the first and second blades 130, 140.

Figure 15:
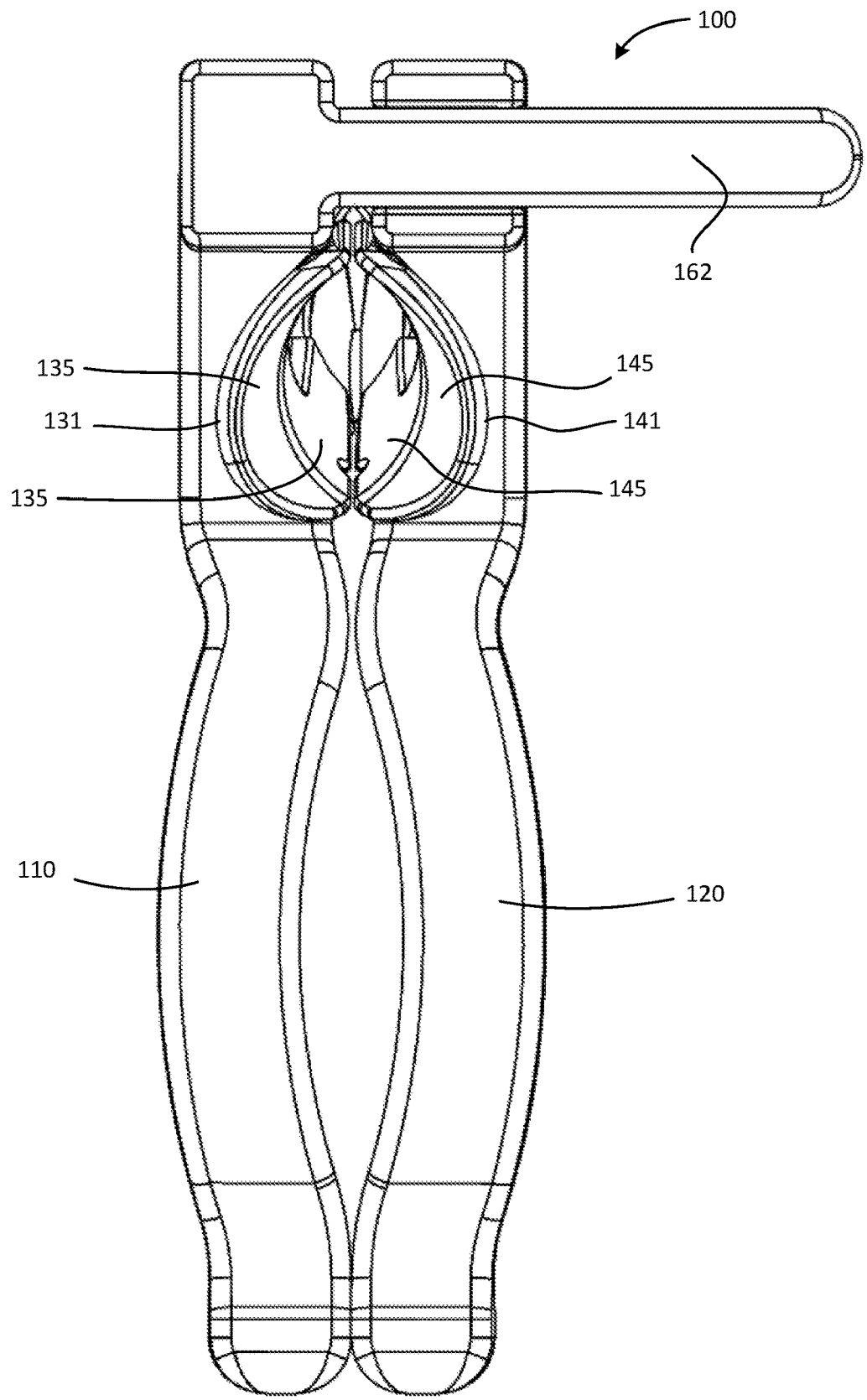
FIG. 15 is a side view of the proximal end of the surgical retractor of FIG. 12.
Figure 16:
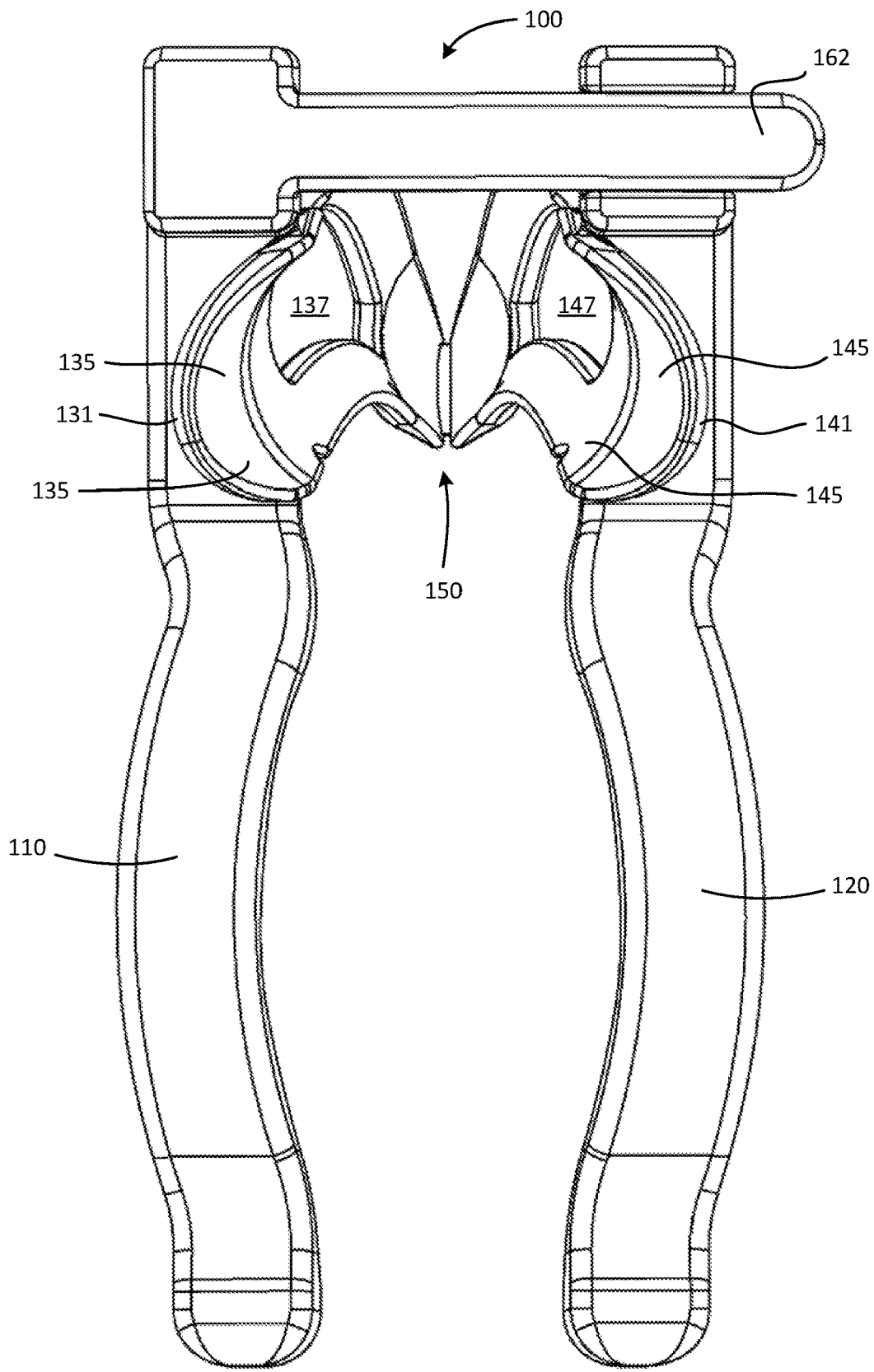
FIG. 16 is a side view of the proximal end of the surgical retractor of FIG. 12 in a retracted position.
Figure 17:
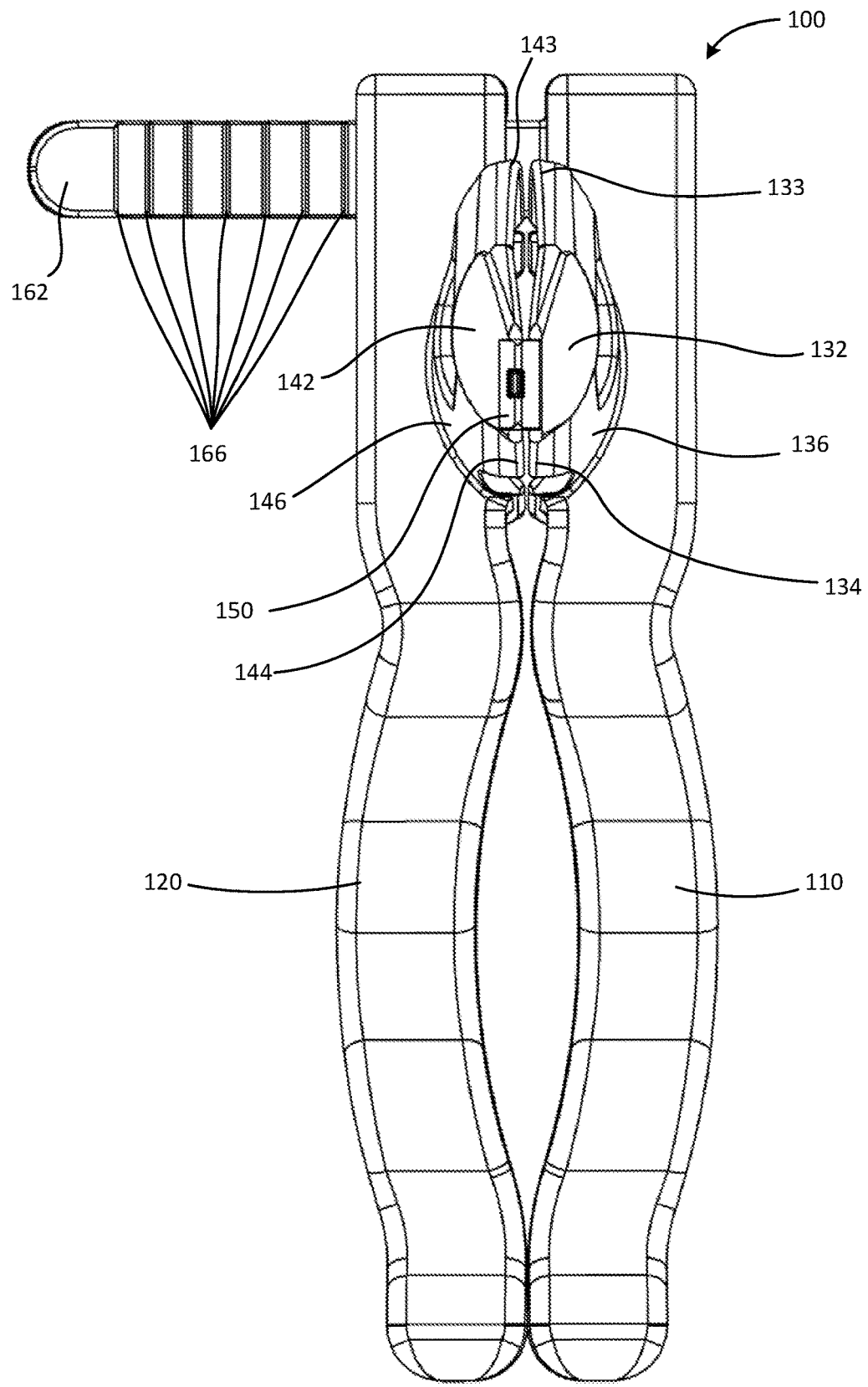
FIG. 17 is a side view of the distal end of the surgical retractor of FIG. 12 in an un-retracted position.
Figure 18:
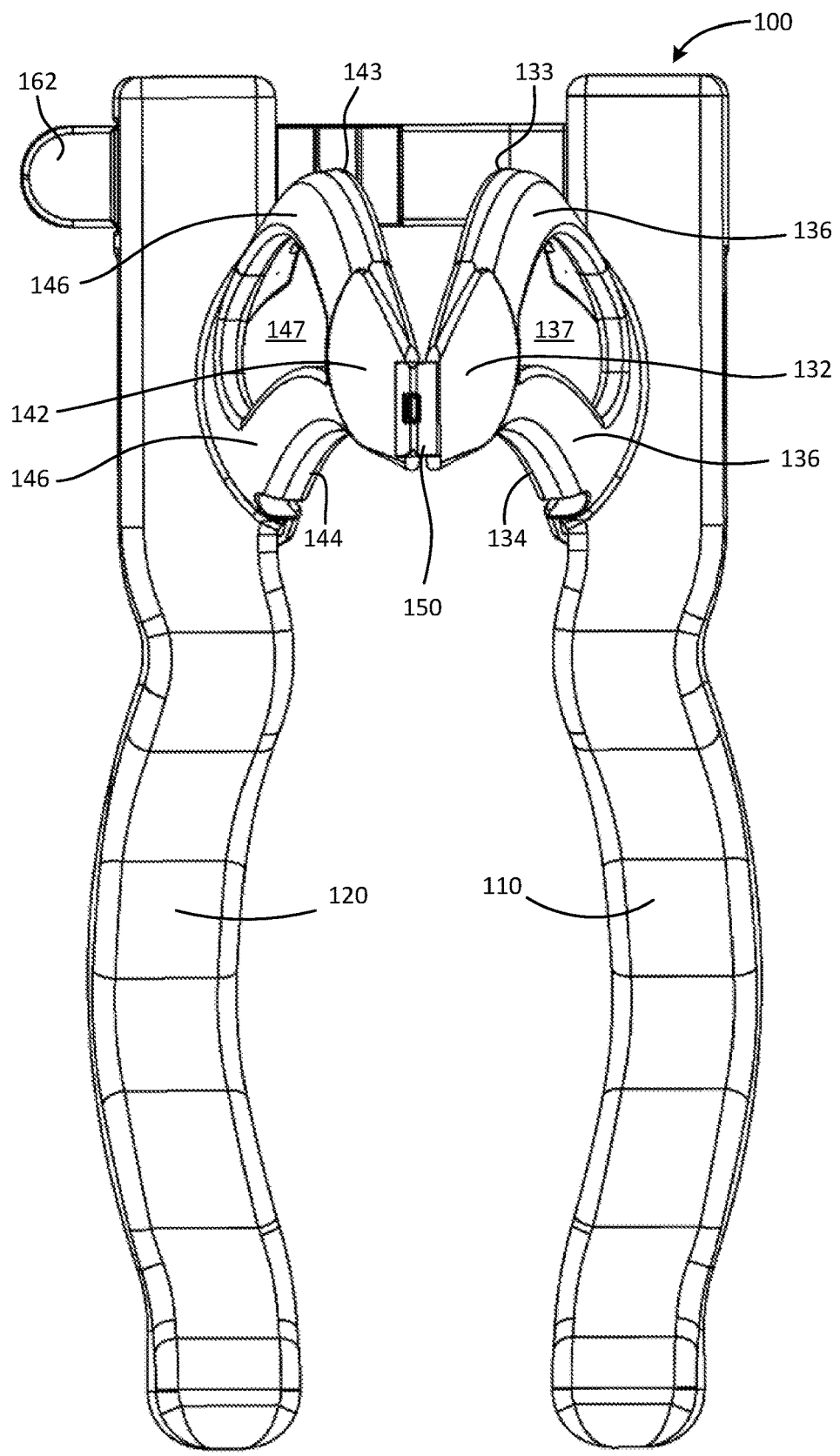
FIG. 18 is a side view of the distal end of the surgical retractor of FIG. 12 in a retracted position.

The first blade 130 may also include a first blade interior surface 135 extending from the proximal end 131 of the first blade 130 to the distal end 132 of the first blade 130, and a first blade exterior surface 136 extending from the proximal end 131 of the first blade 130 to the distal end 132 of the first blade 130. The first blade interior surface 135 may comprises a concave shape, and the first blade exterior surface 136 may comprises a convex shape. Likewise, the second blade 140 may have a second blade interior surface 145 extending from the proximal end 141 of the second blade 140 to the distal end 142 of the second blade 140, and a second blade exterior surface 146 extending from the proximal end 141 of the second blade 140 to the distal end 142 of the second blade 140. The second blade interior surface 145 may comprises a concave shape, and the second blade exterior surface 146 may comprises a convex shape. Moreover, the proximal ends 131, 141 of the first and second blades 130, 140 may extend away from each other to form an enlarged opening between the proximal ends 131, 141 of the first and second blades 130, 140, to allow for greater visibility (as is best shown in FIGS. 15, 16, and 19).

In at least one embodiment, the first blade 130 may further include a first window 137 formed in the first blade 130 and the second blade 140 may also include a second window 147 formed in the second blade 140. The first and second windows 137, 147 may allow for increased tissue visibility and increased access to tissues during a surgical procedure.

The ratcheting mechanism 160 may be configured to maintain a selected distance between the proximal end 131 of the first blade 130 and the proximal end 141 of the second blade 140, as the surgical retractor 100 is selectively moved between an un-retracted position and one of a plurality of different retracted positions.

The ratcheting mechanism 160 may comprise a ratchet arm 162 coupled to the first handle 110 that extends from the first handle 110 toward the second handle 120. The ratchet arm 162 may be received within a channel 164 formed in the second handle 120 (see FIG. 19). The channel 164 may be sized and configured to receive the ratchet arm 162 between a superior channel guide 167 and an inferior channel guide 169. The ratchet arm 162 may also include a plurality of ratchet arm teeth 166, and the channel 164 may include a stop member 168 configured to interact with the plurality of ratchet arm teeth 166. The ratchet arm 162 may also co be configured to apply a bias force that acts to push the ratchet arm teeth 166 toward the stop member 168 once the surgical retractor 100 is fully assembled.

In operation, the surgical retractor 100 may be moved from the un-retracted position to any one of the plurality of different retracted positions by applying opposing forces between the proximal ends 131, 141 of the first and second blades 130, 140 (or between the first and second handles 110, 120) in order to pull apart the proximal ends 131, 141 of the first and second blades 130, 140 such that they move away from each other. In this direction, the "ramp-like" shape of the ratchet arm teeth 166 and the stop member 168 will allow the ratchet arm teeth 166 to slide over the stop member 168 to allow the surgical retractor 100 to move freely toward any one of the plurality of different retracted positions. Once a desired retracted position has been reached, the surgeon may cease applying the opposing forces to the proximal ends 131, 141 of the first and second blades 130, 140, and the stop member 168 will then prevent the surgical retractor 100 from moving backward toward the un-retracted position. In this manner, the ratchet arm teeth 166 biased against the stop member 168 will maintain the selected distance between the proximal end 131 of the first blade 130 and the proximal end 141 of the second blade 140.

In order to move the surgical retractor 100 back toward the un-retracted position from one of the plurality of different retracted positions, the surgeon may simply pull the distal end of the ratchet arm 162 in the proximal direction with a sufficient force that will overcome the bias force of the ratchet arm 162 and disengage the ratchet arm teeth 166 from the stop member 168. The surgeon may also simultaneously apply a compression force (if needed) between the proximal ends 131, 141 of the first and second blades 130, 140 (or between the first and second handles 110, 120) in order to bring the proximal ends 131, 141 of the first and second blades 130, 140 back toward each other.

The hinge 150 may be configured to pivotally couple the distal end 132 of the first blade 130 to the distal end 142 of the second blade 140. As used herein, a "hinge" is broadly defined as any mechanical joint, or any flexible member, that may allow the distal ends 132, 142 of the first and second blades 130, 140 to pivot with respect to each other when the distal ends 132, 142 of the first and second blades 130, 140 are coupled to each other via the hinge.

Figure 21A:
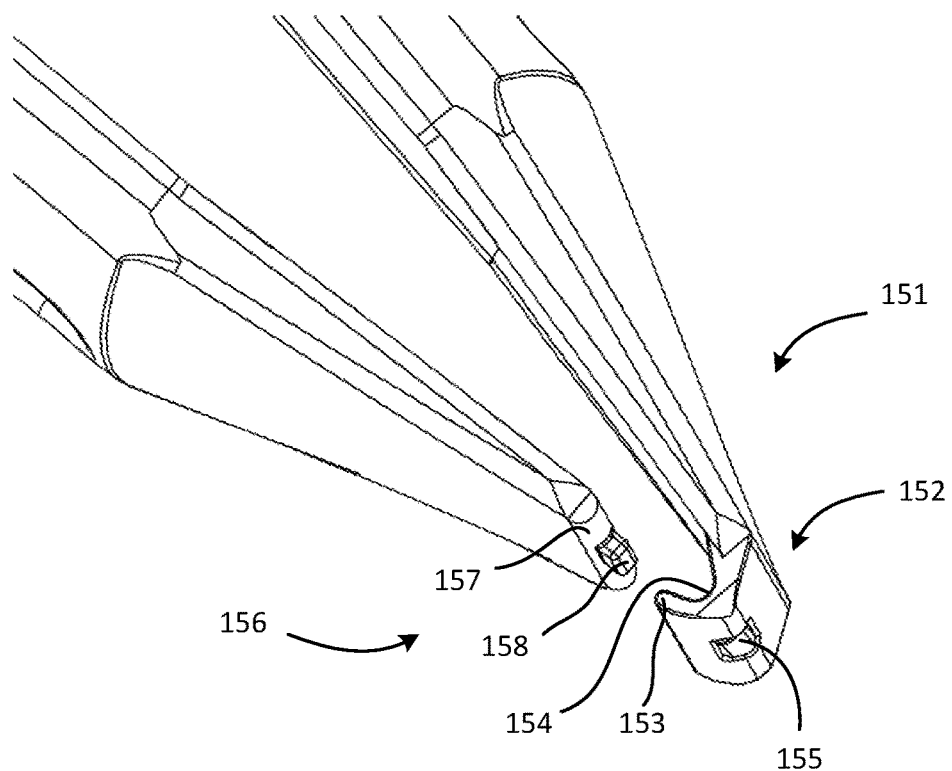
FIG. 21A is a perspective view of the distal end of the surgical retractor of FIG. 12 showing an overlapping hinge design prior to assembly, according to one embodiment of the present disclosure.

FIGS. 21A-24B illustrate various non-limiting examples of hinges that may be used with the surgical retractor 100, according to various embodiments of the present disclosure. FIGS. 21A and 21B show perspective views of an overlapping hinge design; FIGS. 22A and 22B show perspective views of a living hinge design; FIGS. 23A and 23B show perspective views of a pin hinge design; and FIG. 24A show perspective views of an alternative pin hinge design.

Figure 21B:
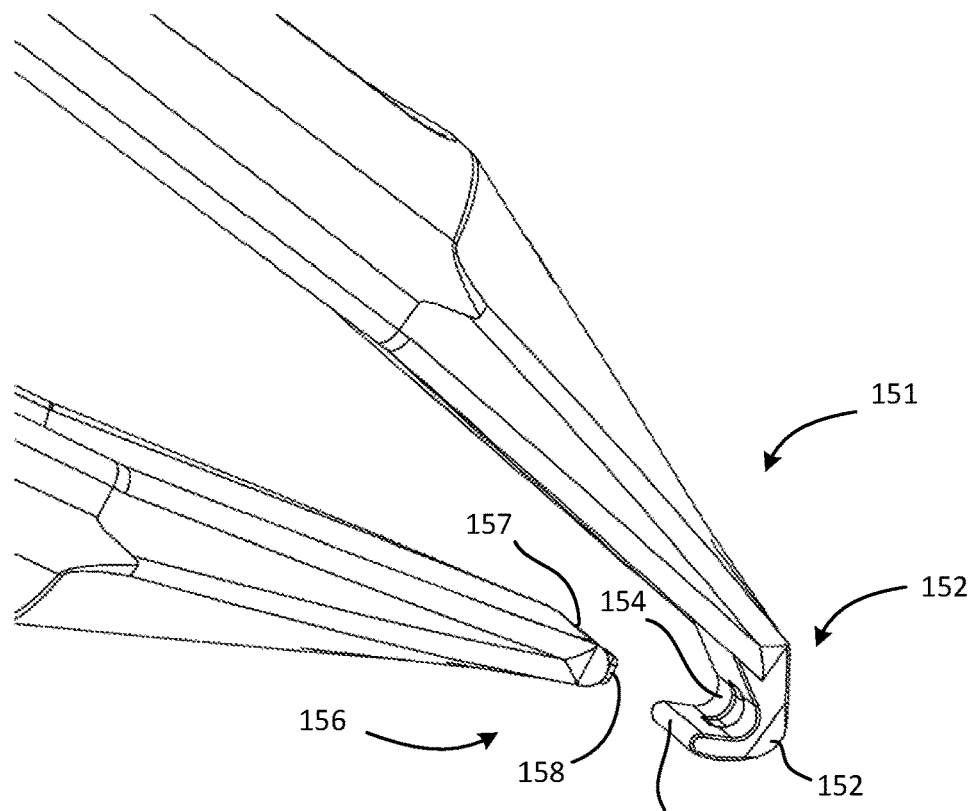
FIG. 21B is another perspective view of the overlapping hinge shown in FIG. 21A.

With reference to FIGS. 21A and 21B, an overlapping hinge 151 is shown, prior to assembly, that may be used to pivotally couple the distal ends 132, 142 of the first and second blades 130, 140 to each other. The overlapping hinge 151 may include a first blade hinge member 152 coupled to the distal end 132 of the first blade 130. The first blade hinge member 152 may extend away from the distal end 132 of the first blade 130, and may comprise a hook projection 153, a first hinge articulating surface 154, and a hinge aperture 155. The overlapping hinge 151 may also include a second blade hinge member 156 coupled to the distal end 142 of the second blade 140. The second blade hinge member 156 may comprise a second hinge articulating surface 157 and a hinge projection 158.

When the overlapping hinge 151 is fully assembled, the concave shape of the first hinge articulating surface 154 is configured to receive the second hinge articulating surface 157 (which comprises a complementary convex shape), in order to pivotally engage the second hinge articulating surface 157 with the first hinge articulating surface 154. Moreover, the hinge aperture 155 formed in the first blade hinge member 152 is configured to receive the hinge projection 158 that extends from the second hinge articulating surface 157 in order to pivotally couple and/or stabilize the overlapping hinge 151 to resist forces that may tend to disassemble the overlapping hinge 151, such as shear forces between the distal ends 132, 142 of the first and second blades 130, 140.

Figure 22A:
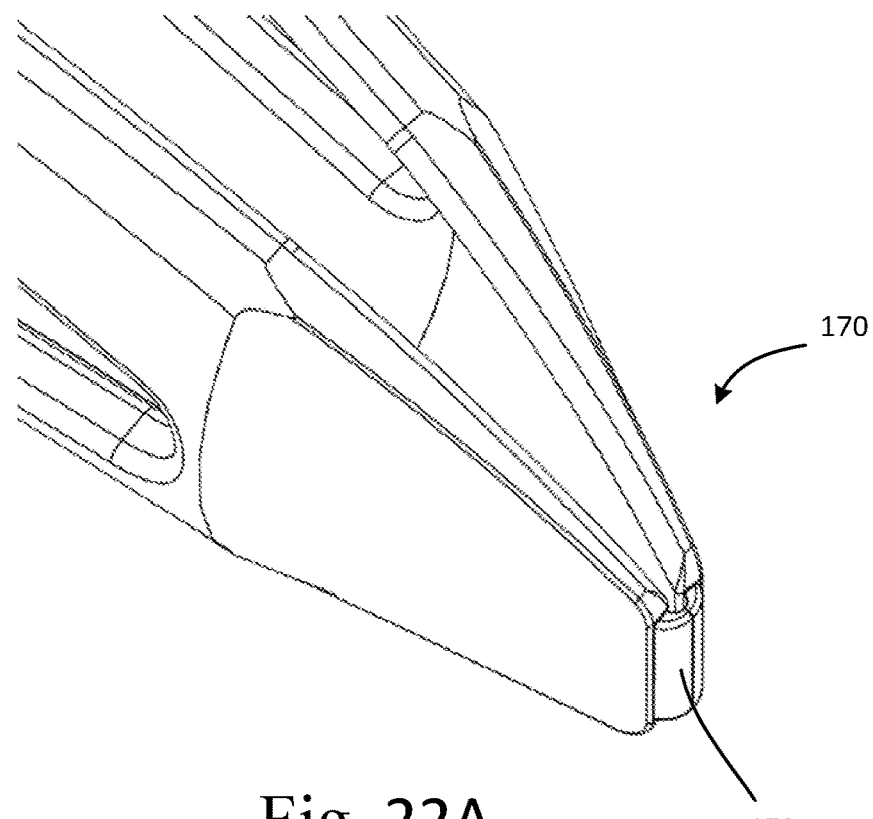
FIG. 22A is a perspective view of the distal end of a surgical retractor with a living hinge design, according to another embodiment of the present disclosure.
Figure 22B:
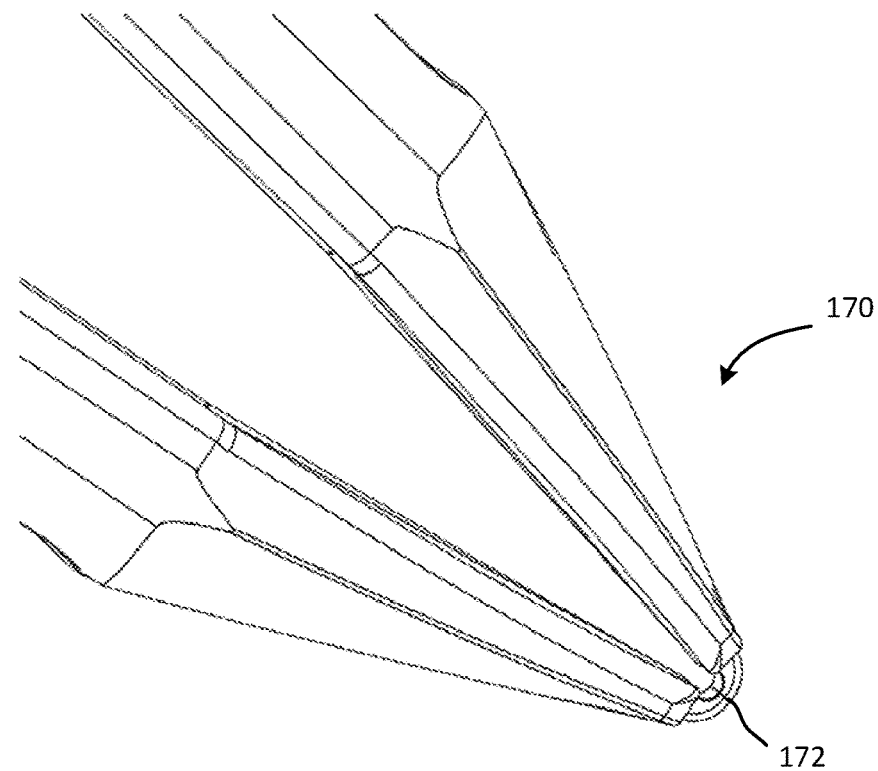
FIG. 22B is another perspective view of the distal end of the surgical retractor of FIG. 22A.

FIGS. 22A and 22B illustrate a living hinge design 170 that may be used to pivotally couple the distal ends 132, 142 of the first and second blades 130, 140 to each other. In at least one embodiment, the living hinge material 172 may be integrally formed with the distal ends 132, 142, of the first and second blades 130, 140. For example, the first and second blades 130, 140 may be integrally formed with the living hinge material 172 during an injection molding process where the surgical retractor 100 is formed from a suitable plastic or metal material (or any other suitable material). In other embodiments, the living hinge material 172 may be separately formed from at least one of the distal ends 132, 142, of the first and second blades 130, 140 and then coupled to one or more of the distal ends 132, 142, of the first and second blades 130, 140. The living hinge material 172 may be configured with any appropriate size, shape, thickness, material properties, etc., in order to achieve a desired resilience, strength, stiffness, etc., for the living hinge material 172.

Figure 23A:
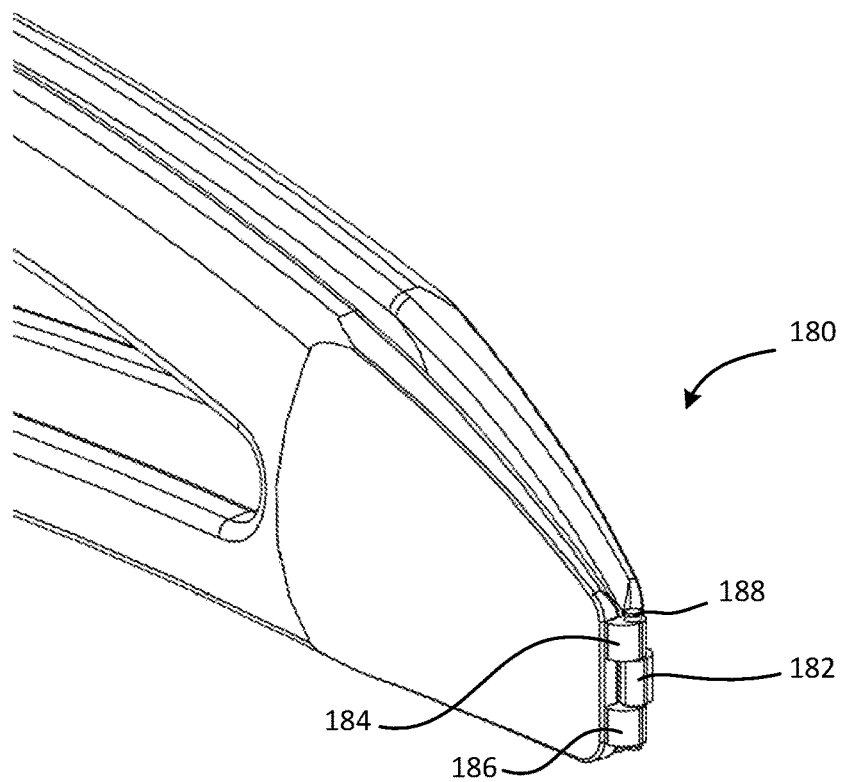
FIG. 23A is a perspective view of the distal end of a surgical retractor with a pin hinge design, according to another embodiment of the present disclosure.
Figure 23B:
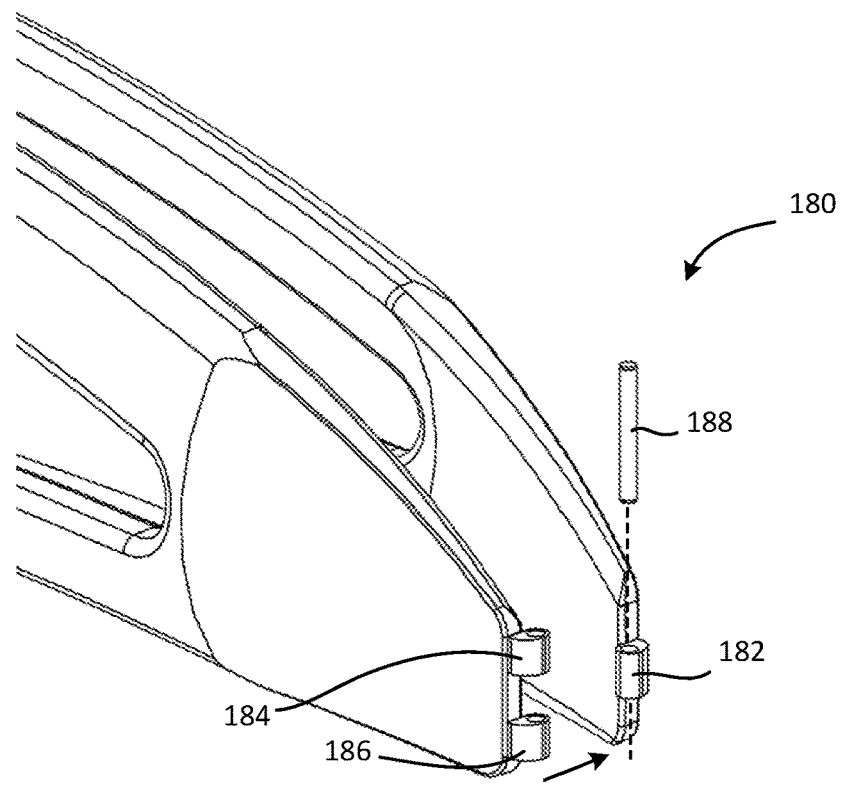
FIG. 23B is an exploded view of the distal end of the pin hinge shown in FIG. 23A.

FIGS. 23A and 23B illustrate a pin hinge 180 design that may be used to pivotally couple the distal ends 132, 142 of the first and second blades 130, 140 to each other. The pin hinge 180 design may include a first pin receiver 182, a second pin receiver 184, a third pin receiver 186, and a pin 188. FIG. 23B illustrates how the first pin receiver 182, the second pin receiver 184, and the third pin receiver 186 may be aligned with each other such that the apertures formed in each of the first, second, and third pin receivers 182, 184, 186 are also aligned with each other and the pin 188 may then be inserted through each of these apertures to pivotally couple the distal ends 132, 142 of the first and second blades 130, 140 to each other.

Figure 24A:
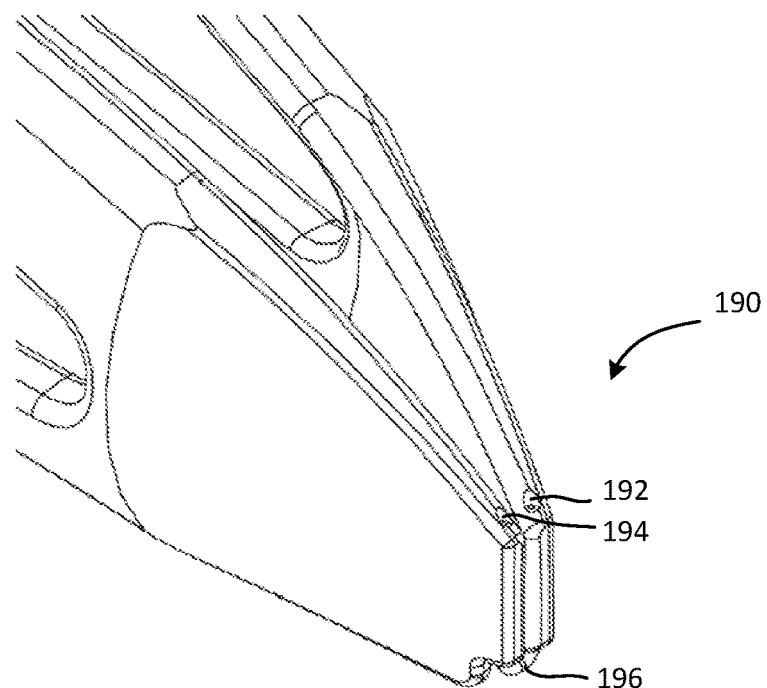
FIG. 24A is a perspective view of the distal end of a surgical retractor with an alternative pin hinge design, according to another embodiment of the present disclosure.
Figure 24B:
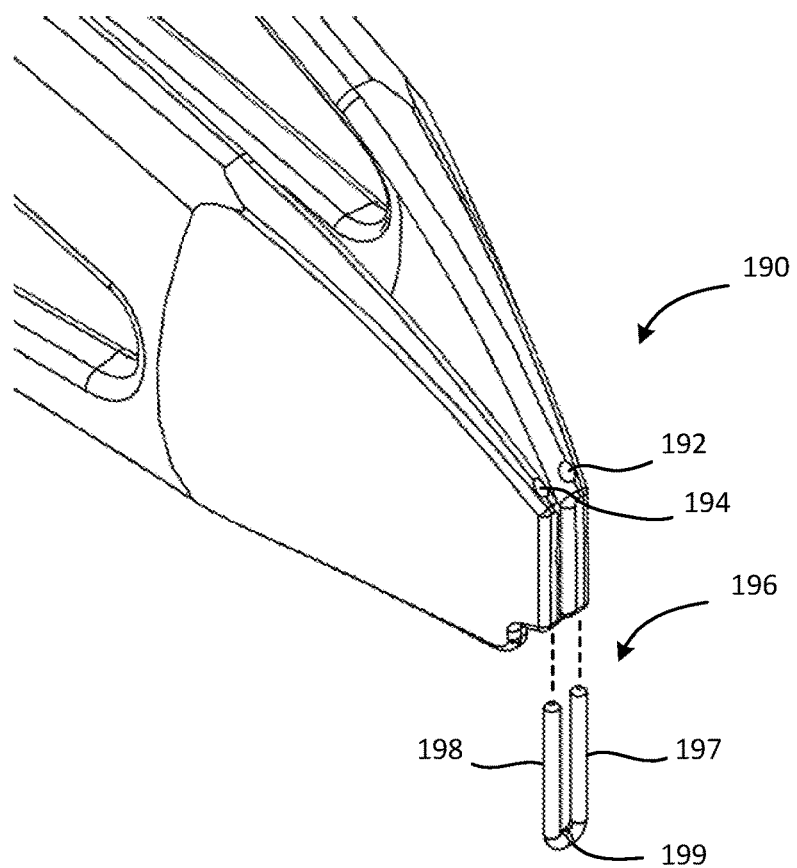
FIG. 24B is an exploded view of the pin hinge shown in FIG. 24A.

FIGS. 24A and 24B illustrate an alternative pin hinge 190 design that may be used to pivotally couple the distal ends 132, 142 of the first and second blades 130, 140 to each other. This alternative pin hinge 190 design may include a first pin aperture 192, a second pin aperture 194, and a U-shaped pin 196 that comprises a first pin leg 197, a second pin leg 198, and a pin elbow 199 that couples the first pin leg 197 to the second pin leg 198. FIG. 24B illustrates how the U-shaped pin 196 may be inserted into the first pin aperture 192 and the second pin aperture 194 to pivotally couple the distal ends 132, 142 of the first and second blades 130, 140 to each other.

Figure 25:
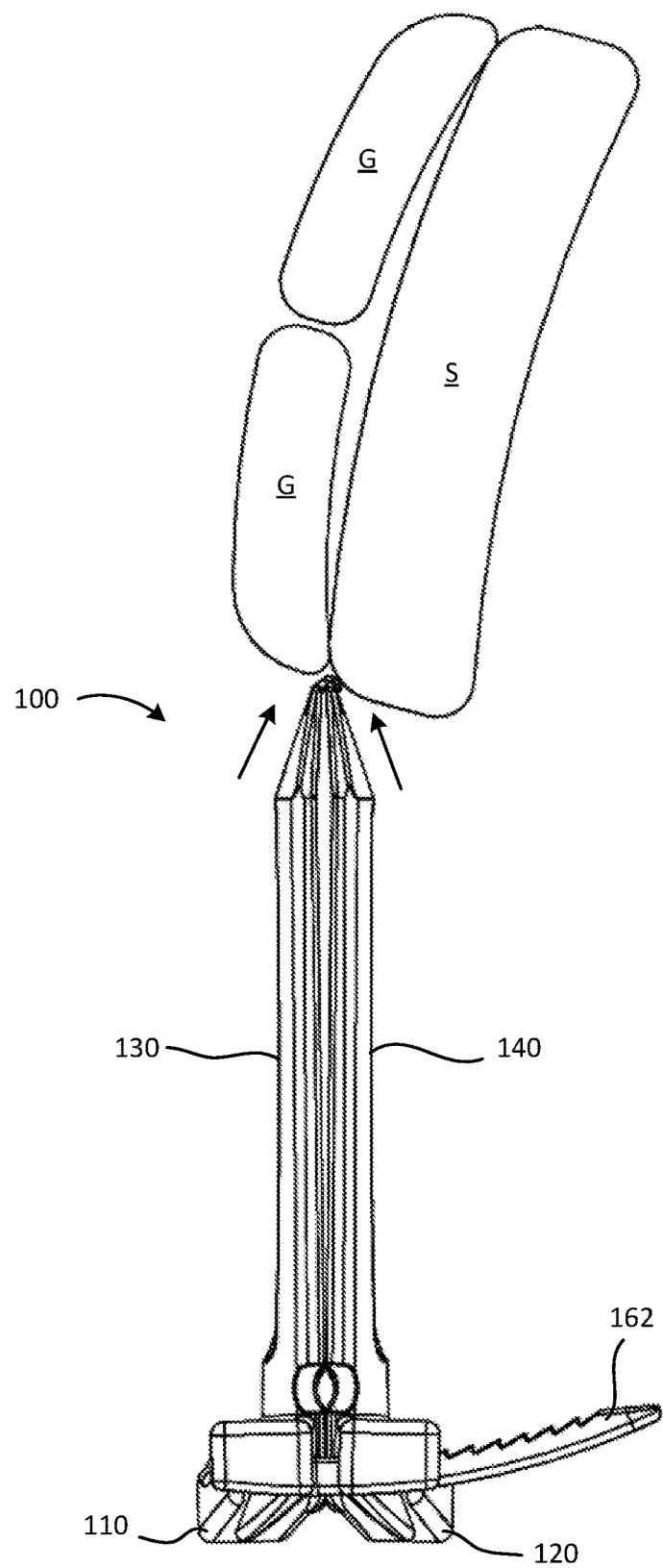
FIG. 25 is a top view of the surgical retractor of FIG. 12, in an un-retracted position, before the surgical retractor is inserted between a soleus muscle and a gastrocnemius muscle.
Figure 26:
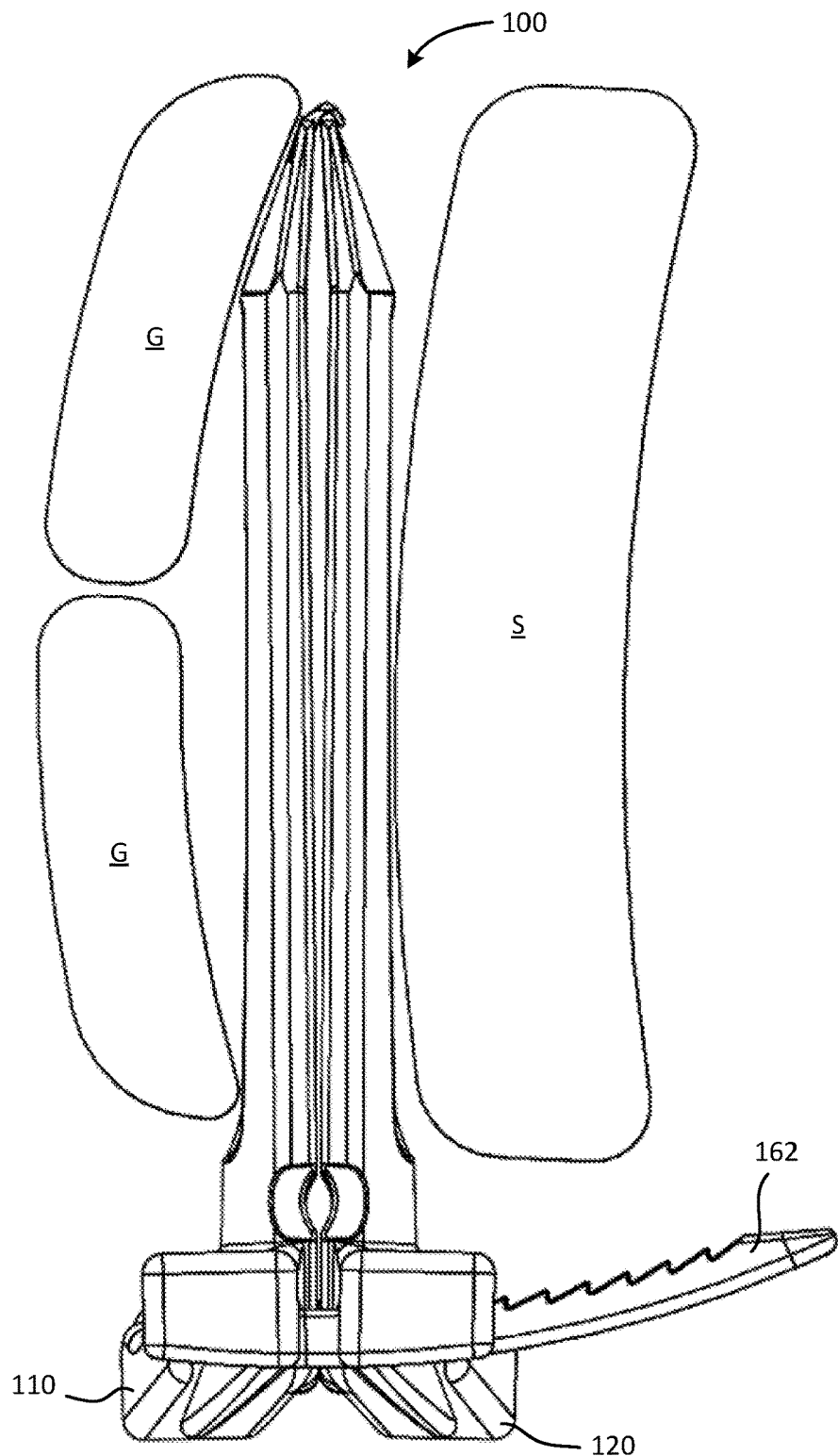
FIG. 26 is a top view of the surgical retractor of FIG. 25 after the surgical retractor has been inserted between the soleus muscle and the gastrocnemius muscle.
Figure 27:
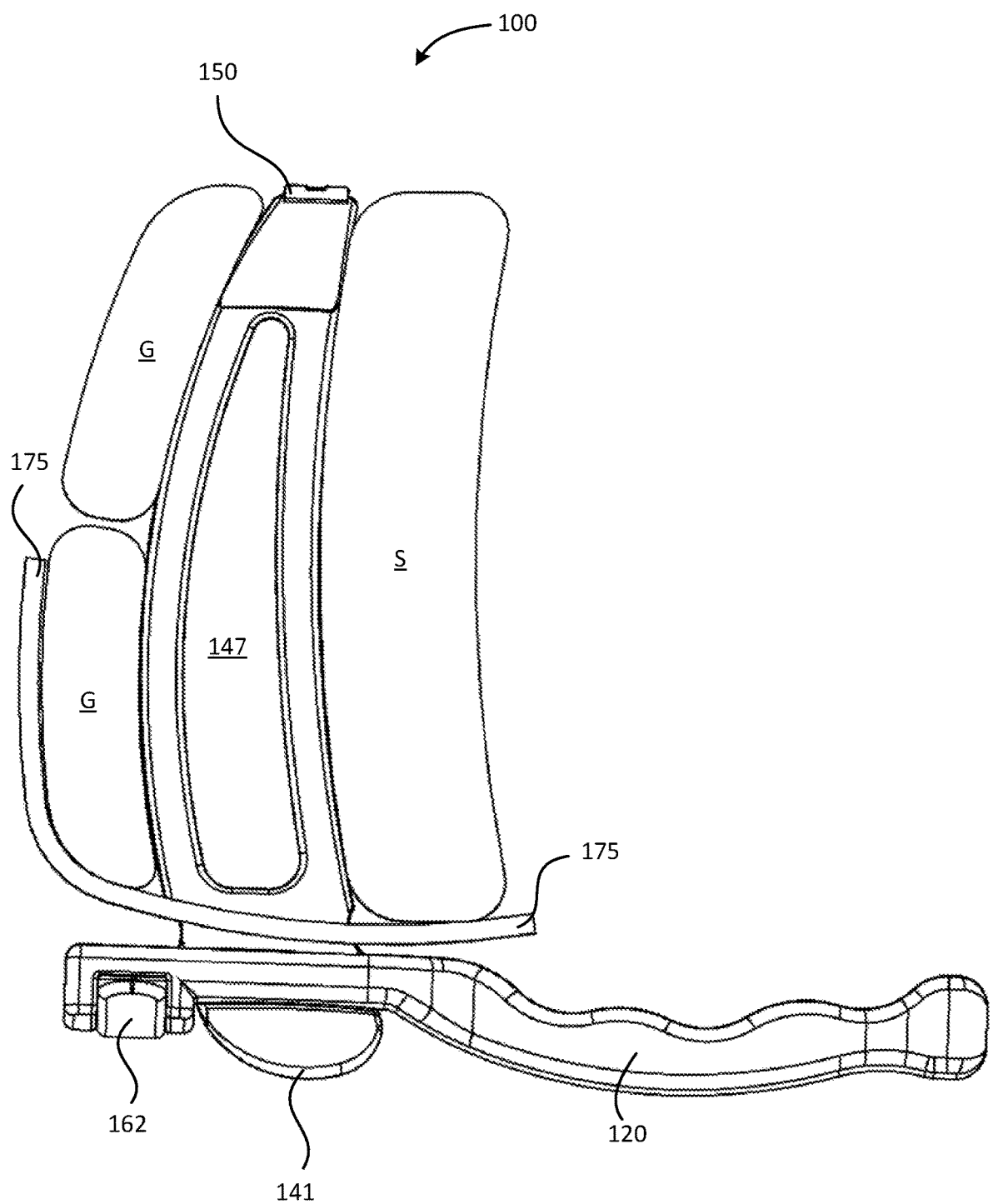
FIG. 27 is a top view of the surgical retractor of FIG. 26 after the surgical retractor has been rotated counter-clockwise (by about 90 degrees) relative to the soleus and gastrocnemius muscles.
Figure 28:
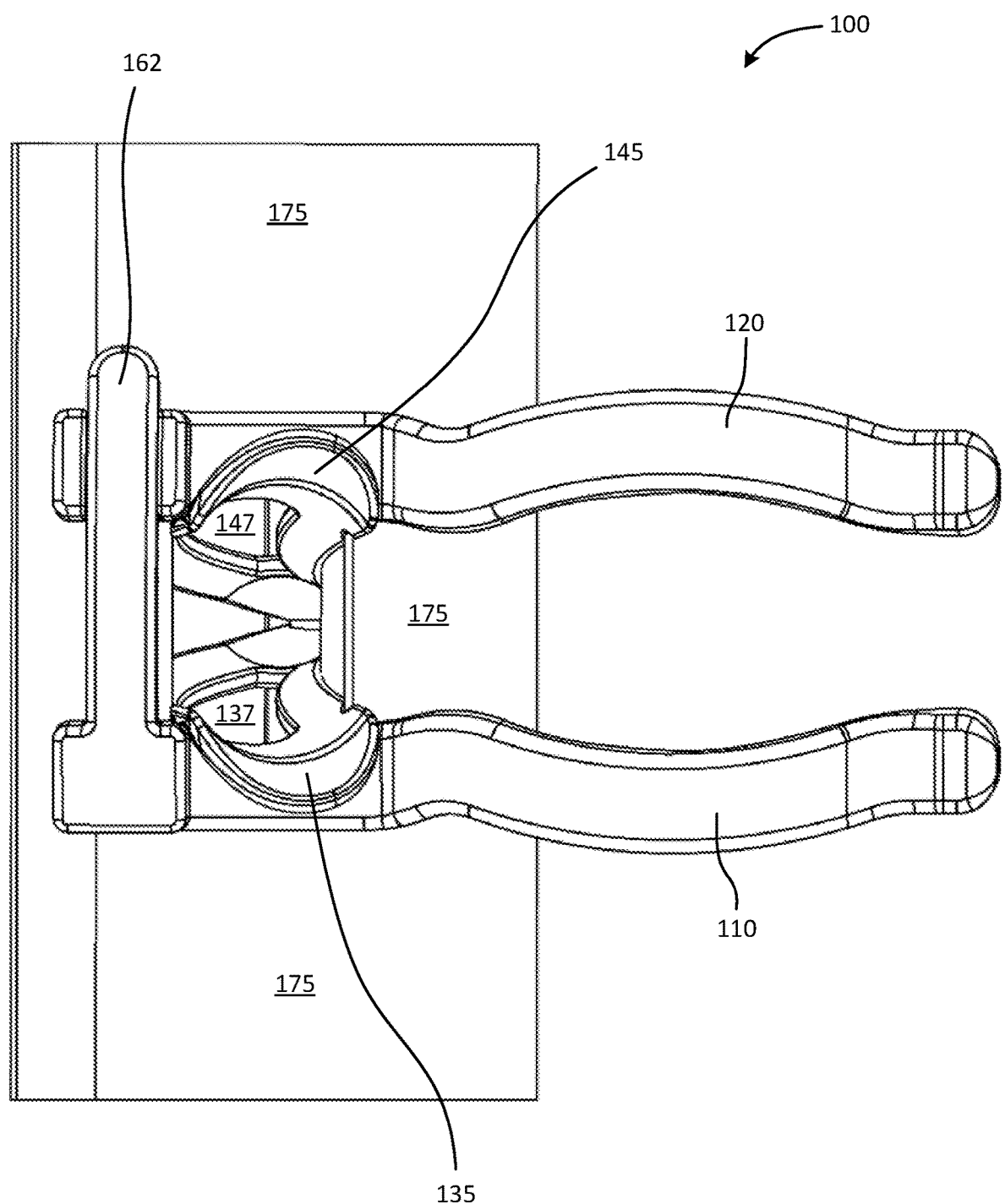
FIG. 28 a side view of the proximal end of the surgical retractor of FIG. 27 after the surgical retractor has been moved from an un-retracted position to a retracted position.
Figure 29:
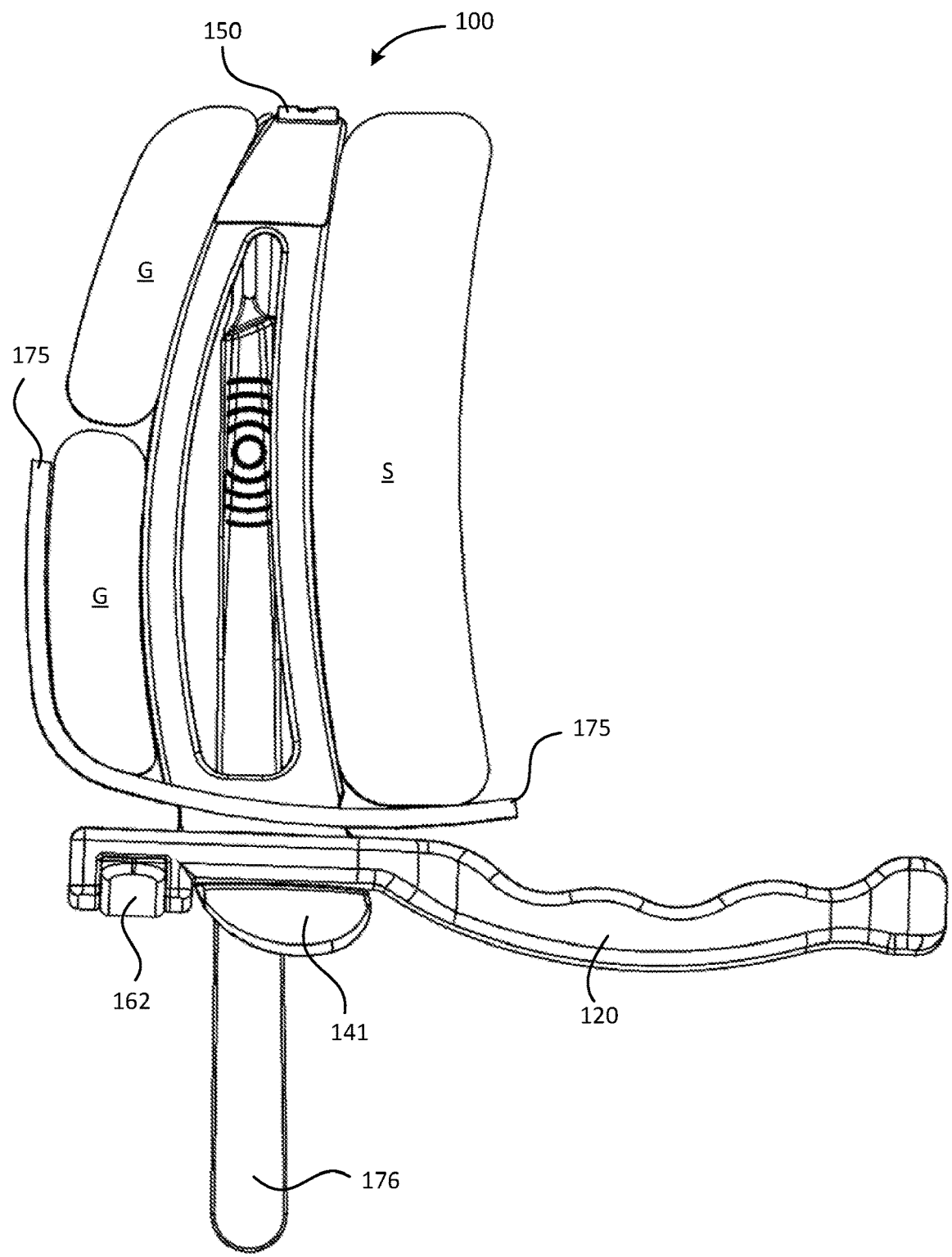
FIG. 29 is a top view of the surgical retractor of FIG. 28 with a scalpel inserted between the retracted soleus and gastrocnemius muscles, in preparation for performing a lengthening procedure on the soleus and/or gastrocnemius muscles.

FIGS. 25-29 illustrate various views of the surgical retractor 100 during an example surgical procedure performed on the soleus S and gastrocnemius G muscles. However, it will be understood that the surgical retractors and concepts described herein may be utilized in any number of different surgical procedures and in any number of different anatomical locations, as previously described herein. FIGS. 25 and 26 are top views of the surgical retractor 100 before and after the surgical retractor 100 has been inserted between the soleus S and gastrocnemius G muscles; FIG. 27 is a top view of the surgical retractor 100 after it has been rotated counter-clockwise (by about 90 degrees) relative to the soleus S and gastrocnemius G muscles; FIG. 28 a side view of the proximal end of the surgical retractor 100 after it has been retracted inside the surgical wound through the skin 175 of the patient; and FIG. 29 is a top view of the surgical retractor 100 with a scalpel 176 inserted into the surgical retractor 100 in preparation for performing a lengthening procedure on the soleus S and/or gastrocnemius G muscles.

Figure 30:
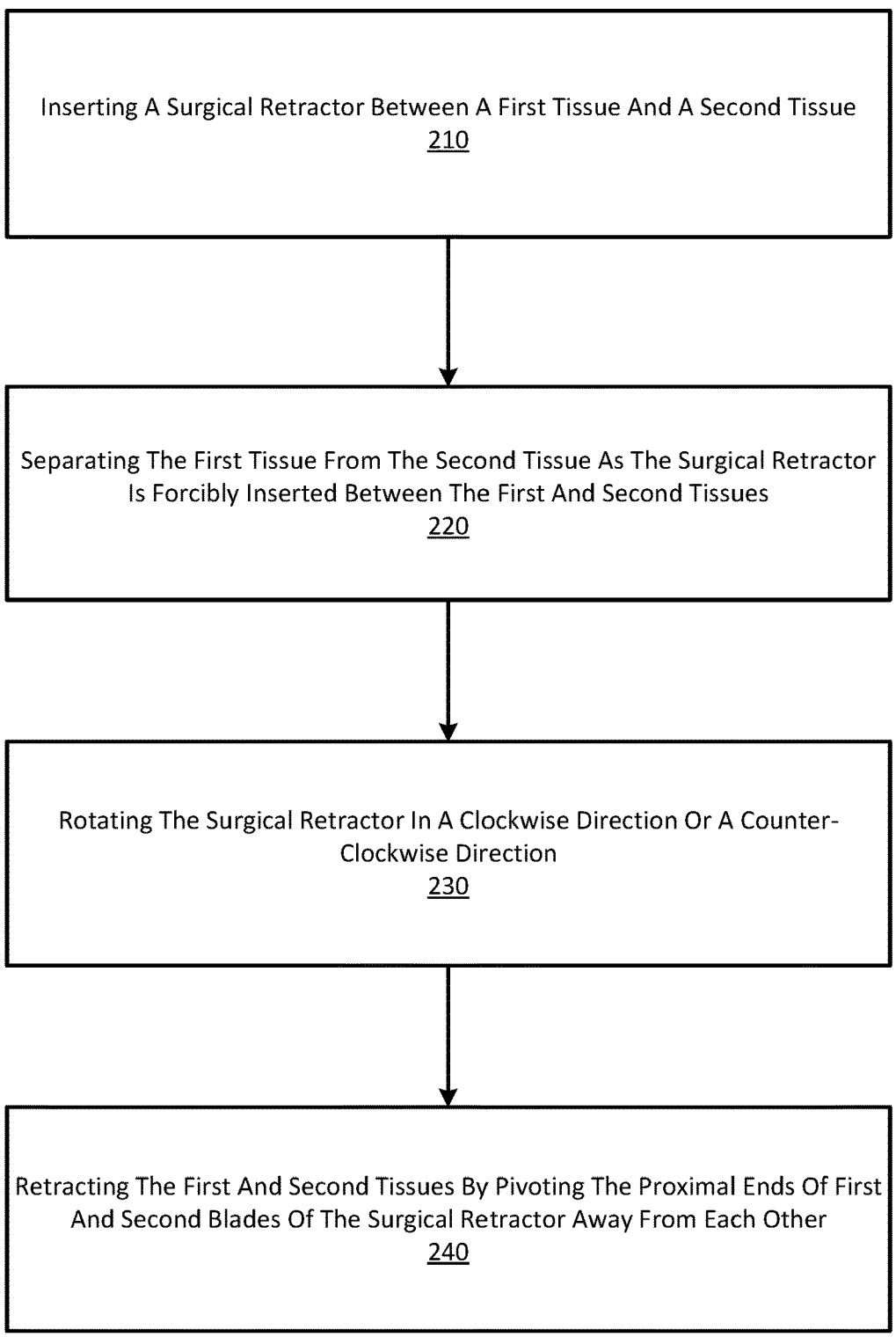
FIG. 30 is a flow chart diagram of a method for retracting tissues with the surgical retractors described herein.

FIG. 30 illustrates a flow chart diagram of a method 200 for retracting tissues with the surgical retractor 100, according to one example of the present disclosure. The method 200 will be described in connection with the surgical retractor 100, as shown in FIGS. 25-29. However, those of skill in the art will recognize that alternative surgical retractors and method steps may be used in the performance of the method 200.

The method 200 may begin with a step 210 in which a surgical retractor may be inserted between a first tissue and a second tissue, such as the soleus S and gastrocnemius G muscles, as shown in FIGS. 25 and 26. The surgical retractor 100 may be presented to the surgical site in an un-retracted position. The distal ends 132, 142 of the first and second blades 130, 140 of the surgical retractor 100 may be placed on a desired insertion point located on the tissues S, G to be retracted. The surgeon may then forcibly insert the first and second blades 130, 140 of the surgical retractor 100 between the first tissue S and the second tissue G, as shown in FIG. 26.

In an optional step 220, the distal ends 132, 142 of the first and second blades 130, 140 of the surgical retractor 100 may be configured to separate the first tissue S from the second tissue G as the distal ends 132, 142 of the first and second blades 130, 140 are forcibly inserted between the first and second tissues S, G. For example, the distal ends 132, 142 of the first and second blades 130, 140 may be configured to be "sharp" enough to separate the first and second tissues from each other as the first and second blades 130, 140 are forcibly inserted into the first and second tissues S, G. However, it will be understood that in some embodiments or surgical procedures, the first and second tissues may already be naturally separated from each other and/or that the first and second tissues may be "pre-separated" by the surgeon in another step (not shown) before the surgical retractor 100 is inserted between the first and second tissues.

Once the surgical retractor 100 has been inserted between the first and second tissues S, G (that have been separated), the method 200 may proceed to an optional method step 230 in which the surgical retractor 100 may be rotated between the first and second tissues S, G in at least one of a clockwise direction and a counter-clockwise direction. In one non-limiting embodiment, the surgical retractor 100 may be rotated within the surgical wound in a counter-clockwise direction by about 90 degrees, as can be seen in FIG. 27. In another non-limiting embodiment, the surgical retractor 100 may be rotated within the surgical wound in a clockwise direction by about 90 degrees (not shown). However, in other embodiments, the surgical retractor 100 may be rotated within the surgical wound in either the clockwise direction or the counter-clockwise direction with any number of degrees of rotation. It will also be understood that method step 230 is optional and, in at least some embodiments, no amount of rotation in either the clockwise or counter-clockwise direction may be desired.

Once the surgical retractor 100 has been rotated between the first and second tissues S, G by a desired amount, the method 200 may proceed to a method step 240 in which the proximal ends 131, 141 of the first and second blades 130, 140 may be pivoted away from each other about a pivot point positioned proximate the distal ends 132, 142 of the first and second blades 130, 140 to retract the first and second tissues S, G away from each other, as shown in FIG. 28, and the method 200 may end.

The various steps of the method 200 disclosed herein may be reordered, omitted, and/or replaced with different steps within the scope of the present disclosure. Those of skill in the art, with the aid of the present disclosure, will recognize that many variations may be made to any method disclosed herein, depending on the particular surgical procedure to be carried out, as well as the configuration of the system used in the performance of that surgical procedure. Moreover, any method disclosed herein may include one or more steps or actions for performing the described method. These method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" may refer to a location on the device that is closest to the clinician using the device and farthest from the patient in connection with whom the device is used when the device is used in its normal operation. Conversely, the term "distal", "bottom", "down" or "downwardly" may refer to a location on the device that is farthest from the clinician using the device and closest to the patient in connection with whom the device is used when the device is used in its normal operation. Moreover, the terms "upper" and "lower", and "top" and "bottom", "front" and "rear" may be used as relative terms herein for ease of description and understanding. It is understood that in embodiments of the disclosure, upper and lower entities may be reversed, as may top and bottom, front and rear.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

The invention claimed is:

1. A surgical retractor comprising:
   a first handle;
   a second handle;
   a first blade coupled to the first handle, the first blade comprising:
      a proximal end;
      a distal end;
      a first blade superior edge extending from the proximal end of the first blade to the distal end of the first blade, the first blade superior edge having a first curvature; and
      a first blade inferior edge, displaced from the first blade superior edge along a superior-inferior direction, extending from the proximal end of the first blade to the distal end of the first blade, the first blade inferior edge having a second curvature; and
   a second blade coupled to the second handle, the second blade comprising:

a proximal end; and
a distal end; and
a hinge configured to pivotally couple the distal end of the first blade to the distal end of the second blade such that the second blade rotates relative to the first blade about an axis extending along the superior-inferior direction,
wherein the first blade superior edge and the first blade inferior edge approach each other moving from the proximal end of the first blade toward the distal end of the first blade.

2. The surgical retractor of claim 1, wherein:
the first blade superior edge extends from the proximal end of the first blade to the distal end of the first blade along a first superior radius; and
the first blade inferior edge extends from the proximal end of the first blade to the distal end of the first blade along a first inferior radius,
wherein the first inferior radius is greater than the first superior radius; and
the second blade comprises:
a second blade superior edge extending from the proximal end of the second blade to the distal end of the second blade along a second superior radius; and
a second blade inferior edge extending from the proximal end of the second blade to the distal end of the second blade along a second inferior radius,
wherein the second inferior radius is greater than the second superior radius.

3. The surgical retractor of claim 1, wherein:
the first blade comprises:
a first blade interior surface extending from the proximal end of the first blade to the distal end of the first blade; and
a first blade exterior surface extending from the proximal end of the first blade to the distal end of the first blade,
wherein the first blade interior surface comprises a concave shape and the first blade exterior surface comprises a convex shape; and
the second blade comprises:
a second blade interior surface extending from the proximal end of the second blade to the distal end of the second blade; and
a second blade exterior surface extending from the proximal end of the second blade to the distal end of the second blade,
wherein the second blade interior surface comprises a concave shape and the second blade exterior surface comprises a convex shape.

4. The surgical retractor of claim 1, wherein the first blade comprises a first window formed in the first blade and the second blade comprises a second window formed in the second blade.

5. The surgical retractor of claim 1, further comprising a ratcheting mechanism, the ratcheting mechanism comprising:
a ratchet arm extending from the first handle toward the second handle; and
a channel formed in the second handle configured to receive the ratchet arm and maintain a selected distance between the proximal end of the first blade and the proximal end of the second blade.

6. The surgical retractor of claim 1, wherein the hinge comprises at least one of:
an overlapping hinge;
a living hinge; and
a pin hinge.

7. The surgical retractor of claim 6, wherein the hinge comprises an overlapping hinge, the overlapping hinge comprising:
a first blade hinge member coupled to the distal end of the first blade and extending from the distal end of the first blade, first blade hinge member comprising:
a first hinge articulating surface comprising a concave shape; and
a hinge aperture formed in the first hinge articulating surface; and
a second blade hinge member coupled to the distal end of the second blade, the second blade hinge member comprising:
a second hinge articulating surface comprising a complementary convex shape configured to be received within the concave shape of the first hinge articulating surface to pivotally engage the second hinge articulating surface with the first hinge articulating surface; and
a hinge projection extending from the second hinge articulating surface, the hinge projection configured to be received within the hinge aperture formed in the first hinge articulating surface to pivotably couple the distal end of the second blade to the distal end of the first blade.

8. A surgical retractor comprising:
a first blade comprising:
a proximal end;
a distal end;
a first blade superior edge extending from the proximal end of the first blade to the distal end of the first blade along a first superior radius; and
a first blade inferior edge extending from the proximal end of the first blade to the distal end of the first blade along a first inferior radius,
wherein the first inferior radius is greater than the first superior radius; and
a second blade comprising:
a proximal end;
a distal end,
the distal end of the first blade pivotally coupled to the distal end of the second blade;
a second blade superior edge extending from the proximal end of the second blade to the distal end of the second blade along a second superior radius; and
a second blade inferior edge extending from the proximal end of the second blade to the distal end of the second blade along a second inferior radius,
wherein the second inferior radius is greater than the second superior radius, and
wherein the first blade superior edge and the first blade inferior edge approach each other moving from the proximal end of the first blade toward the distal end of the first blade, and the second blade superior edge and the second blade inferior edge approach each other moving from the proximal end of the second blade toward the distal end of the second blade; and
a ratcheting mechanism configured to maintain a selected distance between the proximal end of the first blade and the proximal end of the second blade.

9. The surgical retractor of claim 8, wherein:
the first blade comprises:
a first blade interior surface extending from the proximal end of the first blade to the distal end of the first blade; and a first blade exterior surface extending from the proximal end of the first blade to the distal end of the first blade, wherein the first blade interior surface comprises a concave shape and the first blade exterior surface comprises a convex shape; and the second blade comprises:

a second blade interior surface extending from the proximal end of the second blade to the distal end of the second blade; and a second blade exterior surface extending from the proximal end of the second blade to the distal end of the second blade, wherein the second blade interior surface comprises a concave shape and the second blade exterior surface comprises a convex shape, and wherein the first blade comprises a first window formed in the first blade and the second blade comprises a second window formed in the second blade.

10. The surgical retractor of claim 8, wherein the distal end of the first blade is pivotally coupled to the distal end of the second blade by a hinge, the hinge comprising at least one of:

an overlapping hinge;
a living hinge; and
a pin hinge.

11. The surgical retractor of claim 8, wherein the ratcheting mechanism further comprises:

a ratchet arm extending from a first handle coupled to the first blade toward a second handle coupled to the second blade; and a channel formed in the second handle that is configured to receive the ratchet arm and maintain the selected distance between the proximal end of the first blade and the proximal end of the second blade.

12. The surgical retractor of claim 8, wherein the proximal ends of the first and second blades extend away from each other to form an enlarged opening between the proximal ends of the first and second blades.

13. A surgical retractor configured to provide access to tissues during a surgical procedure, the surgical retractor comprising:

a first handle;
a second handle;
a first blade comprising:
  a proximal end coupled directly to the first handle;
  a distal end;
  a first blade exterior surface extending from the proximal end of the first blade to the distal end of the first blade;
a second blade comprising:
  a proximal end coupled directly to the second handle;
  a distal end;
  a second blade exterior surface extending from the proximal end of the second blade to the distal end of the second blade; and
a hinge configured to pivotally couple the distal end of the first blade to the distal end of the second blade, wherein, in an unretracted position, the hinge and distal ends of the first and second blade exterior surfaces comprise a sharp shape configured to separate a first tissue from a second tissue.

14. The surgical retractor of claim 13, wherein:

the first blade comprises:

a first blade superior edge extending from the proximal end of the first blade to the distal end of the first blade along a first superior radius; and a first blade inferior edge extending from the proximal end of the first blade to the distal end of the first blade along a first inferior radius, wherein the first inferior radius is greater than the first superior radius; and the second blade comprises:

a second blade superior edge extending from the proximal end of the second blade to the distal end of the second blade along a second superior radius; and a second blade inferior edge extending from the proximal end of the second blade to the distal end of the second blade along a second inferior radius, wherein the second inferior radius is greater than the second superior radius.

15. The surgical retractor of claim 13, wherein:

the first blade comprises:

a first blade interior surface extending from the proximal end of the first blade to the distal end of the first blade, wherein the first blade interior surface comprises a concave shape and the first blade exterior surface comprises a convex shape; and the second blade comprises:

a second blade interior surface extending from the proximal end of the second blade to the distal end of the second blade, wherein the second blade interior surface comprises a concave shape and the second blade exterior surface comprises a convex shape.

16. The surgical retractor of claim 13, wherein the first blade comprises a first window formed in the first blade and the second blade comprises a second window formed in the second blade.

17. The surgical retractor of claim 13, further comprising a ratcheting mechanism, the ratcheting mechanism comprising:

a ratchet arm extending from a first handle of the surgical retractor toward a second handle of the surgical retractor; and a channel formed in the second handle configured to receive the ratchet arm and maintain a selected distance between the proximal end of the first blade and the proximal end of the second blade.

18. The surgical retractor of claim 13, wherein the hinge comprises at least one of:

an overlapping hinge;
a living hinge; and
a pin hinge.

* * * * *